United States Patent
Kimura et al.

(10) Patent No.: US 10,098,563 B2
(45) Date of Patent: Oct. 16, 2018

(54) MAGNETIC RESONANCE IMAGING APPARATUS

(75) Inventors: Tokunori Kimura, Yaita (JP); Masato Ikedo, Otawara (JP)

(73) Assignee: TOSHIBA MEDICAL SYSTEMS CORPORATION, Otawara-Shi, Tochigi-Ken (JP)

(*) Notice: Subject to any disclaimer, the term of this patent is extended or adjusted under 35 U.S.C. 154(b) by 394 days.

(21) Appl. No.: 11/943,765

(22) Filed: Nov. 21, 2007

(65) Prior Publication Data
US 2008/0119721 A1    May 22, 2008

(30) Foreign Application Priority Data

Nov. 22, 2006 (JP) ................. 2006-315823
Apr. 27, 2007 (JP) ................. 2007-119883

(51) Int. Cl.
| A61B 5/055 | (2006.01) |
| A61B 5/00 | (2006.01) |
| G01R 33/50 | (2006.01) |
| G01R 33/56 | (2006.01) |

(Continued)

(52) U.S. Cl.
CPC .............. *A61B 5/055* (2013.01); *A61B 5/417* (2013.01); *A61B 5/489* (2013.01); *G01R 33/5635* (2013.01); *G01R 33/50* (2013.01); *G01R 33/5601* (2013.01); *G01R 33/5607* (2013.01); *G01R 33/5608* (2013.01); *G01R 33/5616* (2013.01); *G01R 33/56308* (2013.01)

(58) Field of Classification Search
CPC .... A61B 5/417; A61B 5/489; G01R 33/5635; G01R 33/5608; G01R 33/5616; G01R 33/50; G01R 33/5601

USPC .......................................... 600/410, 420, 431
See application file for complete search history.

(56) References Cited

U.S. PATENT DOCUMENTS

| 4,731,583 A * | 3/1988 | Glover ............. G01R 33/56509 324/309 |
| 5,001,429 A | 3/1991 | Constable et al. |
| 5,034,694 A * | 7/1991 | Sattin et al. .................. 324/309 |

(Continued)

FOREIGN PATENT DOCUMENTS

| CN | 1497254 A | 5/2004 |
| CN | 1635855 A | 7/2005 |

(Continued)

OTHER PUBLICATIONS

Kellman, Peter et al. Multicontrast Delayed Ehancement Provides Imrpoved Contrast Between Myocardial Infarction and Blood Pool. Journal of Magnetic Resonance Imaging, 22:605-613 (2005).*

(Continued)

*Primary Examiner* — Michael Kahelin
*Assistant Examiner* — Helene Bor
(74) *Attorney, Agent, or Firm* — Nixon & Vanderhye P.C.

(57) ABSTRACT

A magnetic resonance imaging apparatus includes an acquisition unit which acquires first data in which a tissue of interest has higher signal intensity than a background and second data in which the tissue of interest has lower signal intensity than the background, with regard to images of the same region of the same subject, and a generation unit which generates, on the basis of the first data and the second data, third data in which the contrast of the tissue of interest to the background is higher than those in the first and second data.

10 Claims, 16 Drawing Sheets

(51) Int. Cl.
*G01R 33/561* (2006.01)
*G01R 33/563* (2006.01)

(56) References Cited

U.S. PATENT DOCUMENTS

| | | | | |
|---|---|---|---|---|
| 5,331,279 | A * | 7/1994 | Hatanaka | 324/306 |
| 5,353,794 | A | 10/1994 | Miyazaki | |
| 5,521,502 | A * | 5/1996 | Siegel, Jr. | G01F 1/704 |
| | | | | 324/306 |
| 5,602,891 | A * | 2/1997 | Pearlman | 378/62 |
| 5,602,934 | A | 2/1997 | Li et al. | |
| 5,671,264 | A * | 9/1997 | Florent | G06T 5/20 |
| | | | | 250/369 |
| 5,771,893 | A | 6/1998 | Kassai et al. | |
| 5,897,496 | A | 4/1999 | Watanabe | |
| 6,002,254 | A | 12/1999 | Kassai et al. | |
| 6,340,887 | B1 | 1/2002 | Liu et al. | |
| 6,442,414 | B1 | 8/2002 | Watanabe | |
| 6,501,272 | B1 | 12/2002 | Haacke et al. | |
| 6,658,280 | B1 | 12/2003 | Haacke | |
| 6,891,373 | B2 | 5/2005 | Deimling | |
| 7,847,545 | B2 | 12/2010 | Wiesinger et al. | |
| 2003/0171671 | A1* | 9/2003 | Miyazaki | G01R 33/563 |
| | | | | 600/420 |
| 2006/0074285 | A1* | 4/2006 | Zarkh et al. | 600/407 |

FOREIGN PATENT DOCUMENTS

| | | |
|---|---|---|
| JP | 61-88132 | 5/1986 |
| JP | 64-65439 | 3/1989 |
| JP | 4-141143 | 5/1992 |
| JP | 4-200445 | 7/1992 |
| JP | 4-292142 | 10/1992 |
| JP | 5-184555 | 7/1993 |
| JP | 7-184879 | 7/1995 |
| JP | 10-75937 | 3/1998 |
| JP | 10-248825 | 9/1998 |
| JP | 11-244257 | 9/1999 |
| JP | 2001-204708 | 7/2001 |
| JP | 2001-327480 | 11/2001 |
| JP | 2002-28149 | 1/2002 |
| JP | 2002-510537 | 4/2002 |
| JP | 2002-143125 | 5/2002 |
| JP | 2002-515772 | 5/2002 |
| JP | 2002-177240 | 6/2002 |
| JP | 2002-200054 | 7/2002 |
| JP | 2002-263082 | 9/2002 |
| JP | 2004-57237 | 2/2004 |
| JP | 2004-129724 | 4/2004 |
| JP | 2005-198715 | 7/2005 |
| JP | 2006-223869 | 8/2006 |
| JP | 2008-125891 | 6/2008 |
| WO | 00/65995 | 9/2000 |
| WO | 00/65995 | 11/2000 |

OTHER PUBLICATIONS

Miyazaki, Mitsue et al. Peripheral MR Angiography: Separation of Arteries from Veins with Flow-spoiled Gradient Pulses in Electrocardiography-triggered Three-dimensional Half-Fourier Fast Spin-Echo Imaging. vol. 227, Issue 3: Jun. 2003.*
Office Action dated Feb. 6, 2009 in CN 200710169350.0 with English translation.
Haacke et al., "Susceptibility Weighted Imaging (SWI)", *Magnetic Resonance in Medicine*, vol. 52, 2004, pp. 612-618.
Reichenberg et al., "High-Resolution MR Venography at 3.0 Tesla", *Journal of Computer Assisted Tomography*, vol. 24, No. 6, 2000, pp. 949-957.
JP Office Action in JP 2012-034340 dated Sep. 24, 2013 with English translation.
JP Office Action in JP 2008-275500 dated Oct. 8, 2013 with English translation.
K. C. Goodrich, et al., "Comparison of three MRA registration techniques," Proc. Intl. Soc. Mag. Reson. Med. 12, May 2004, p. 2240.
Office Action in JP 2007-119883 dated Dec. 20, 2011 with English translation.
Office Action in JP 2006-315823 dated Nov. 8, 2011 with English translation.
Günther, Matthias et al., "Arterial Spin Labeling in Combination With a Look-Locker Sampling Strategy: Inflow Turbo Sampling EPI-FAIR (ITS-FAIR)," Magnetic Resonance in Medicine, Nov. 2001,, vol. 46, No. 5, pp. 974-984.
Office Action dated Jul. 31, 2012 in JP 2007-119883 with English translation.
Final Office Action dated Apr. 2, 2013 in JP 2007-119883 with English translation.
First Office Action dated Apr. 2, 2013 in JP 2012-034340 with English translation.
Office Action dated Mar. 18, 2014 in JP 2013-117269 and English translation.
Office Action dated Feb. 4, 2016 in U.S. Appl. No. 12/888,239.
Office Action dated Jan. 21, 2016 in U.S. Appl. No. 12/292,527.
Jon-Fredrik Nielsen et al., "SSFP and GRE Phase Contrast Imaging Using a Three-Echo Readout," Magn. Reson. Med. Dec. 2007; 58(6): 1288-1293.
Office Action dated Oct. 5, 2016 in U.S. Appl. No. 12/888,239.
Bitar, Richard et al., "MR Pulse Sequences: What Every Radiologist Wants to Know but is Afraid to Ask," Radiographics, vol. 26, No. 2; 2006.
Office Action dated Sep. 14, 2017 in U.S. Appl. No. 12/888,239.
Wang, Yi et al., "A Three-Point Dixon Method for Water and Fat Separation Using 2D and 3D Gradient-Echo Techniques," Journal of Magnetic Resonance Imaging, May-Jun. 1998; 8(3): 703-10.
Office Action dated Jun. 6, 2018 in U.S. Appl. No. 12/888,239.

* cited by examiner

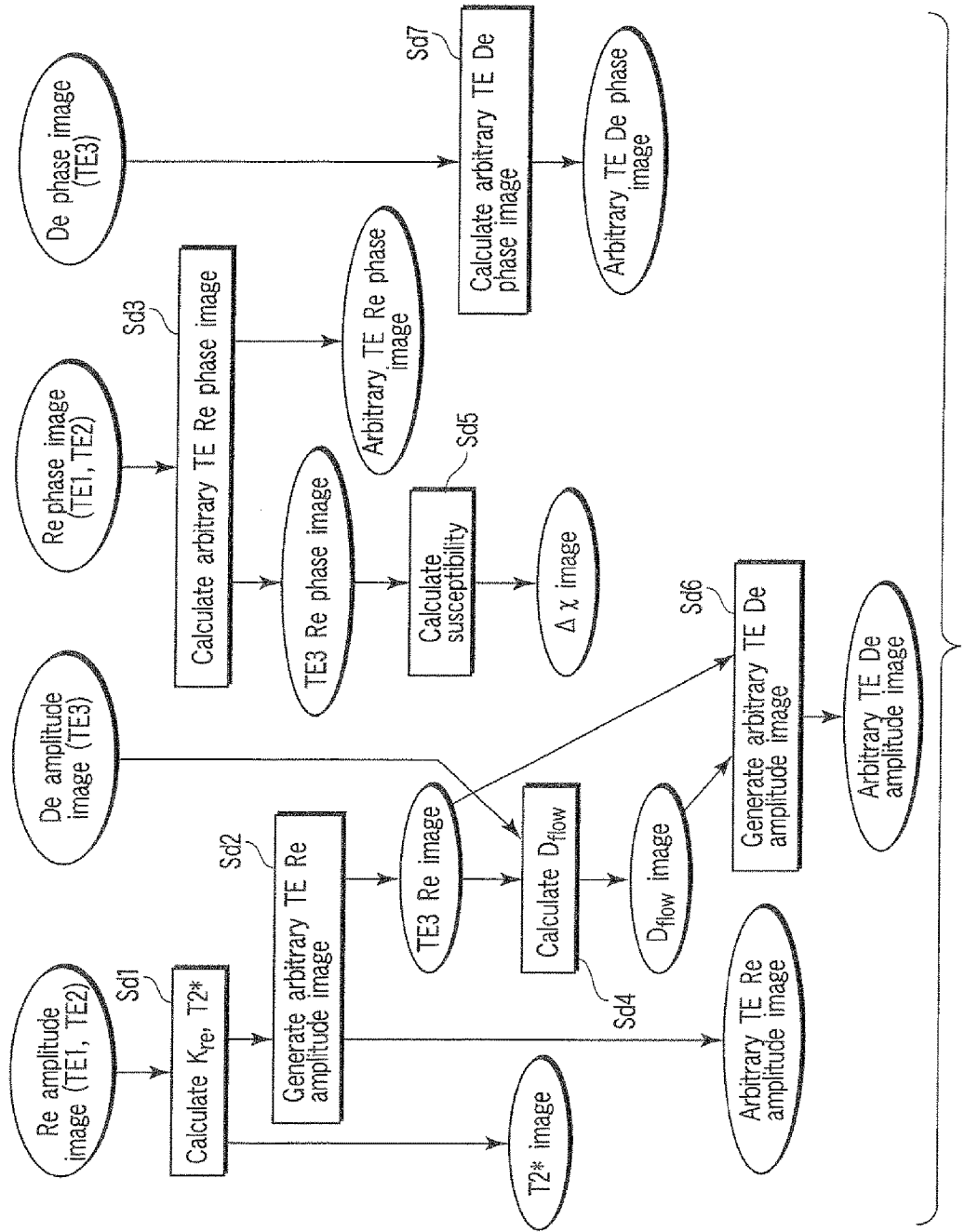
F I G. 19

Asymmetric type $M(\phi) = (1/\pi)\phi + 1 : 0 <= \phi < \pi$
$\quad\quad = 1 : -\pi <= \phi < 0$ Symmetric type $M(\phi) = (1/\pi)\phi + 1 : -\pi <= \phi < 0$
$\quad\quad = -(1/\pi)\phi + 1 : 0 <= \phi < \pi$

MAGNETIC RESONANCE IMAGING APPARATUS

CROSS-REFERENCE TO RELATED APPLICATIONS

This application is based upon and claims the benefit of priority from prior Japanese Patent Applications No. 2006-315823, filed Nov. 22, 2006; and No. 2007-119883, filed Apr. 27, 2007, the entire contents of both of which are incorporated herein by reference. This application is also related to CIP application Ser. No. 12/292,527 filed Nov. 20, 2008 (now U.S. Pat. No. 9,538,936 issued Jan. 10, 2017), and to divisional application Ser. No. 12/888,239 filed Sep. 22, 2010.

BACKGROUND

1. Technical Field

The present invention relates to a magnetic resonance imaging apparatus which obtains information for medical diagnoses on the basis of a magnetic resonance signal emitted from a subject.

2. Related Art

MR angiography (MRA) is a magnetic resonance imaging method intended for arteries and veins. MRA includes a time of flight (TOF) method using a gradient echo (GRE) method, and a black-blood (BB) method using a fast spin echo (FSE) method for visualizing a blood vessel at low signal intensity. Recently, a susceptibility-weighted imaging (SWI) method which applies the susceptibility effect of veins has been devised (refer to the specification of U.S. Pat. No. 6,501,272).

A non-contrast TOF method is a typical example of a white-blood method. The non-contrast TOF method utilizes an inflow effect, so that an artery with a high flow velocity close to an inflow part of a slab is visualized at high signal intensity. In this non-contrast TOF method, it is difficult to visualize turbulent parts, and peripheral blood vessels such as perforating branches are not easily visualized. In other words, arteries are principally visualized in the non-contrast TOF method.

Furthermore, when an image is taken with a T1W-based sequence using a paramagnetic contrast medium, blood vessels are visualized at high signal intensity, which means a WB method. In addition, an MRA method in which blood vessels show higher signal intensity than background tissues is widely referred to as the WB method here.

In the BB method, blood vessels show lower signal intensity than peripheral tissues. In the BB method, low blood flows are also visualized, and blood vessel walls are correctly visualized. It is also possible in the BB method to visualize the turbulent parts which are difficult to visualize in the TOF method. The FSE method was initially used in a sequence of the BB method, but is not used very widely due to the problem of image processing, or other problems. In the BB method, while both arteries and veins show low signal intensity, the arteries can be highlighted by setting an echo time (TE) slightly shorter. In addition, when an image is taken with a T2*W based sequence using the paramagnetic contrast medium, blood vessels are visualized at low signal intensity, which means the BB method.

In the BB method, peripheral tissues also show low signal intensity, and it is therefore difficult to separately visualize the blood vessels alone. For example, it is difficult to exclude air by minimum intensity projection (minIP) in the BB method. The visualization of blood vessels in the WB method can be relatively easily carried out by, for example, maximum intensity projection (MIP).

The above-mentioned conventional MRA has advantages and disadvantages in both the WB method and the BB method, and these methods are suitably used in accordance with purposes. However, it has been difficult in both the WB method and the BB method to clearly visualize various structures of blood vessels.

On the other hand, methods for collecting magnetic resonance signals include a method in which a spin is dephased and a method in which a spin is rephased. These two collection methods are selectively used in accordance with purposes. Thus, information for medical diagnoses can be obtained on the basis of the magnetic resonance signals collected in one of these methods.

Another technique has been known in which information obtained on the basis of magnetic resonance signals collected in one of the methods is subjected to different processing to obtain useful information. For example, as an imaging method more sensitive to a change in the magnetic susceptibility owing to T2* enhancement, there has been proposed a technique which carries out phase emphasizing processing for an absolute value image reconstructed on the basis of magnetic resonance signals collected by rephase (refer to Magn. Reson. Med. 52:612-618, 2004.).

However, there is a limit to information that can be obtained from the magnetic resonance signals collected by dephase or rephase, therefore it has been impossible to obtain information necessary to satisfactorily visualize, for example, blood vessels.

BRIEF SUMMARY

Under such circumstances, there has been a demand to obtain an image clearly showing various structures of a tissue of interest such as a blood vessel.

On the other hand, there has been a desire to obtain useful information which has not been obtained from magnetic resonance signals independently collected by dephase or rephase.

According to a first aspect of the present invention, there is provided a magnetic resonance imaging apparatus comprising: an acquisition unit which acquires first data in which a tissue of interest has higher signal intensity than a background and second data in which the tissue of interest has lower signal intensity than the background, with regard to images of the same region of the same subject; and a generation unit which generates, on the basis of the first data and the second data, third data in which the contrast of the tissue of interest to the background is higher than those in the first and second data.

According to a second aspect of the present invention, there is provided a magnetic resonance imaging apparatus comprising: an acquisition unit which acquires first data in which a tissue of interest has a higher signal intensity than a background and second data in which the tissue of interest has a lower signal intensity than the background, with regard to images of the same region of the same subject; and a generation unit which generates third data indicating an image, the image being a composition of an image indicated by the first data and an image indicated by the second data to which different colors are allocated.

According to a third aspect of the present invention, there is provided a magnetic resonance imaging apparatus comprising: a scan unit which executes, with regard to a region of interest of a subject, a first scan for data collection by a pulse sequence to obtain first image data in which blood vessel has a higher signal intensity than a background, and a second scan for collection by a pulse sequence different from that of the first scan to obtain second image data in which the blood vessel has a higher signal intensity than the background; and a generation unit which generates, on the basis of the first image data and the second image data, third image data in which the contrast of the blood vessel to the background is higher than those in the first and second image data.

According to a fourth aspect of the present invention, there is provided a magnetic resonance imaging apparatus comprising: a scan unit which executes, with regard to a region of interest of a subject, a first scan for data collection by a pulse sequence to obtain first image data in which blood vessel has a lower signal intensity than a background, and a second scan for collection by a pulse sequence different from that of the first scan to obtain second image data in which the blood vessel has a lower signal intensity than the background; and a generation unit which generates, on the basis of the first image data and the second image data, third image data in which the contrast of the blood vessel to the background is higher than those in the first and second image data.

According to a fifth aspect of the present invention, there is provided a magnetic resonance imaging apparatus comprising: a collection unit which collects magnetic resonance signals emitted from a subject; a reconstruction unit which reconstructs at least one dephase image and at least one rephase image on the basis of the collected magnetic resonance signals; and a quantification unit which quantifies characteristics regarding the subject on the basis of both the reconstructed dephase image and rephase image.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 19 is a diagram showing the flow of analytic parameter image calculating processing in the case of collecting two points for the rephase TE and one point for the dephase TE;

DETAILED DESCRIPTION OF EXEMPLARY EMBODIMENTS

Embodiments of the present invention will be hereinafter described with reference to the drawings.

Figure 1:
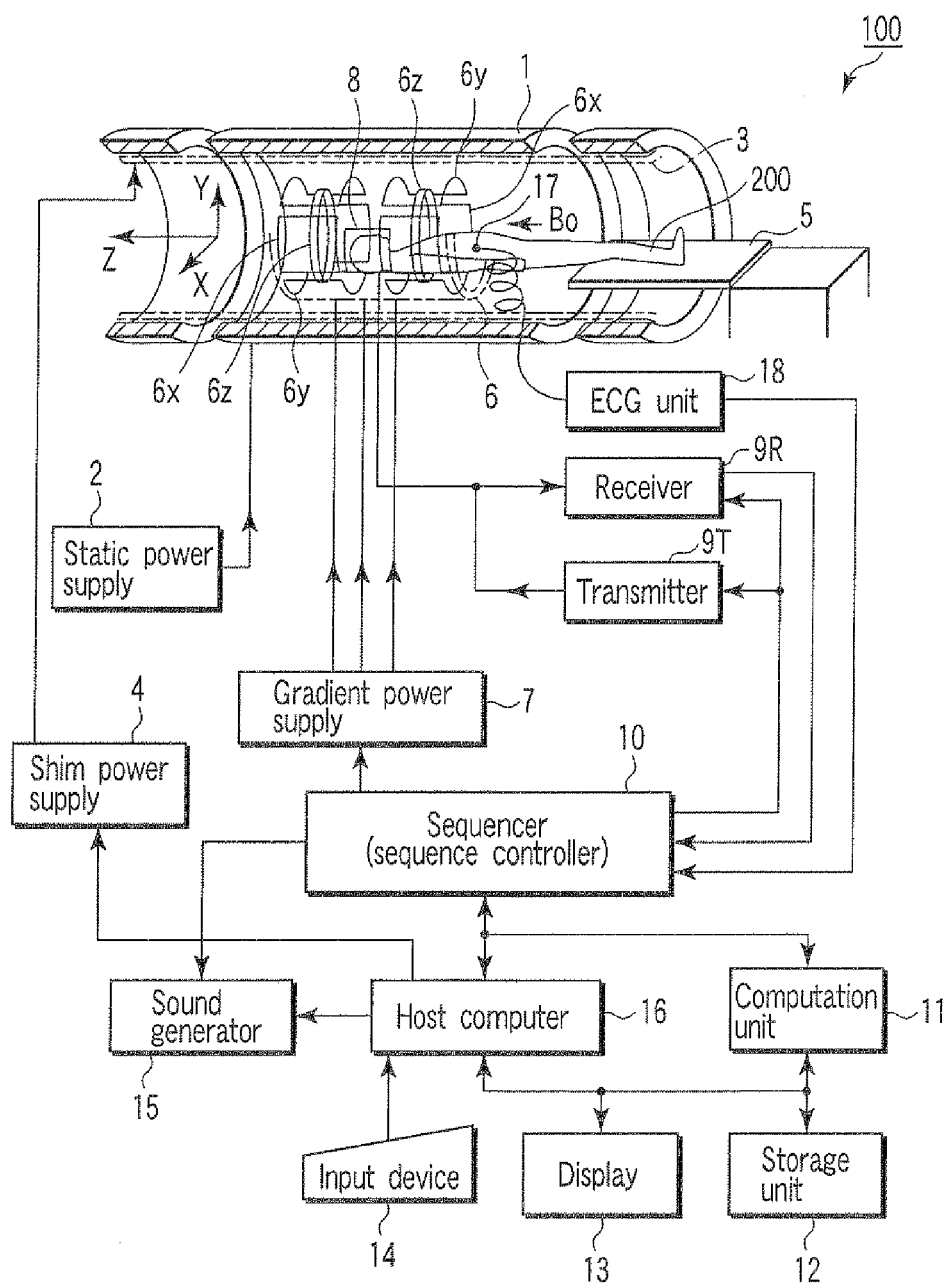
FIG. 1 is a diagram showing the schematic configuration of a magnetic resonance imaging apparatus (MRI apparatus) according to embodiments of the present invention.

FIG. 1 is a diagram showing the schematic configuration of a magnetic resonance imaging apparatus (MRI apparatus) 100 according to the present embodiments.

The MRI apparatus 100 comprises a bed unit, a static-magnetic-field generating unit, a gradient-magnetic-field generating unit, a receiving/transmitting unit, and a control/operating unit. The bed unit moves a subject 200 mounted thereon. The static-magnetic-field generating unit generates a static magnetic field. The gradient-magnetic-field generating unit generates a gradient magnetic field designed to add position information to the static magnetic field. The receiving/transmitting unit receives and transmits a radio-frequency signal. The control/operating unit controls the whole system and reconstructs images. The MRI apparatus 100 has, as components of these units, a magnet 1, a static magnetic power supply 2, a shim coil 3, a shim power supply 4, a top plate 5, a gradient coil unit 6, a gradient power supply 7, an RF coil unit 8, a transmitter 9T, a receiver 9R, a sequencer (sequence controller) 10, an computation unit 11, a storage unit 12, a display 13, an input device 14, a sound generator 15, and a host computer 16. Connected to the MRI apparatus 100 is an electrocardiograph unit which measures an ECG signal as a signal representing the cardiac pulsation of the subject 200.

The static-magnetic-field generating unit includes the magnet 1, the static magnetic power supply 2, the shim coil 3 and the shim power supply 4. For example, a superconducting magnet or a normal conducting magnet can be used as the magnet 1. The static magnetic power supply 2 supplies a current to the magnet 1. In addition, the static magnetic power supply 2 can be omitted when the superconducting magnet is employed as the magnet 1. The static-magnetic-field generating unit therefore generates a static magnetic field $B_0$ in a cylindrical space (diagnostic space) into which the subject 200 is moved. The direction of the static magnetic field $B_0$ virtually coincides with the axial direction (Z-axis direction) of the diagnostic space. The shim coil 3 generates a correction magnetic field for rendering the static magnetic field uniform when a current is supplied to it from the shim power supply 4 under the control of the host computer 16.

The bed unit moves the top plate 5, on which the subject 200 is lying, into or out of the diagnostic space.

The gradient-magnetic-field generating unit includes the gradient coil unit 6 and the gradient power supply 7. The gradient coil unit 6 is arranged in the magnet 1. The gradient coil unit 6 has three coils 6x, 6y and 6z that generate gradient magnetic fields extending in mutually orthogonal X-, Y- and Z-axes, respectively. The gradient power supply 7 supplies pulse currents for generating gradient magnetic fields to the coils 6x, 6y and 6z, under the control of the sequencer 10. The gradient-magnetic-field generating unit controls the pulse currents supplied from the gradient power supply 7 to the coils 6x, 6y and 6z. Thus, the gradient-magnetic-field generating unit synthesizes gradient magnetic fields extending in the three physical axes (the X-, Y- and Z-axes), respectively. The unit sets these magnetic fields in logical axes defined by a slice direction gradient magnetic field Gs, a phase-encode direction gradient magnetic field Ge and a read-out direction (frequency-encode) gradient magnetic field Gro, respectively, which intersect at right angles with one another. The slice, phase-encode and read-out direction gradient magnetic fields, Gs, Ge and Gr are superposed on the static magnetic field $B_0$.

The receiving/transmitting unit includes the RF coil unit 8, the transmitter 9T, and the receiver 9R. The RF coil unit 8 is arranged in the vicinity of the subject 200 in the diagnostic space. The transmitter 9T and the receiver 9R are connected to the RF coil unit 8. The transmitter 9T and the receiver 9R operate under the control of the sequencer 10. The transmitter 9T supplies an RF current pulse of Larmor frequency to the RF coil unit 8 in order to induce nuclear magnetic resonance (NMR). The receiver 9R acquires an MR signal (radio-frequency signal), such as an echo signal, which the RF coil unit 8 has received. The receiver 9R then performs, on the MR signal, various processes, such as pre-amplification, intermediate-frequency conversion, phase detecting, low-frequency amplification and filtering. Finally, the receiver 9R performs analog-to-digital (A/D) conversion on the MR signal, producing digital data (raw data).

The control/operating unit includes the sequencer 10, the computation unit 11, the storage unit 12, the display 13, the input device 14, the sound generator 15 and the host computer 16.

The sequencer 10 has a CPU and a memory. The sequencer 10 stores, into the memory, pulse sequence information transmitted from the host computer 16. The CPU of the sequencer 10 controls the operations of the gradient power supply 7, transmitter 9T and receiver DR in accordance with the sequence information stored in the memory. The CPU of the sequencer 10 also receives the raw data output from the receiver 9R and transfers the raw data to the computation unit 11. Note that the sequence information is all data necessary for operating the gradient power supply 7, transmitter 9T and receiver 9R in accordance with the pulse sequence. It includes, for example, information about the intensity of the pulse current supplied to the coils 6x, 6y and 6z, the period of applying the pulse current and the timing of applying the pulse current.

The computation unit 11 receives the raw data output from the transmitter 9T, through the sequencer 10. The computation unit 11 has an internal memory. The internal memory has a k-space (also called Fourier space or frequency space), in which the raw data input to the computation unit 11 is placed. The computation unit 11 subjects the data placed in the k-space to two- or three-dimensional Fourier transform, thereby reconstructing video data for the real space. The computation unit 11 can perform, if necessary, synthesis and differential operations (including weighted differentiation) on any data representing an image. The synthesis includes cumulative addition of pixel values, maximum intensity projection (MIP), minimum intensity projection (minIP), and the like. As another example of the synthesis, the axes of several frames may be aligned in a Fourier space, and the raw data items representing these frames may be synthesized, thereby generating one-frame raw data. The addition of pixel values includes, for example, simple addition, addition averaging or weighting addition.

The storage unit 12 stores video data reconstructed or video data subjected to the above-mentioned synthesis or differential processing.

The display 13 displays various images to be presented to a user, under the control of the host computer 16. For example, a display device such as a liquid crystal display can be used as the display 13.

The input device 14 is operated to input various types of information, such as parameter information for selecting synchronization timing desired by the operator, scanning conditions, the pulse sequence, information about the image synthesis and differential operation, and the like. The input device 14 sends the input information to the host computer 16. The input device 14 comprises, as the case may be, a pointing device such as a mouse or a track ball, a selection device such as a mode change switch, or an input device such as keyboard.

The sound generator 15 generates messages for the start and end of breath holding as sounds when instructed by the host computer 16.

The host computer 16 controls the operation of every unit of the MRI apparatus 100 to achieve various operations achieved by existing MRI apparatuses. The host computer 16 additionally has a function to set a scaling factor when hybrid MRA is performed as described later.

The electrocardiograph unit includes an ECG sensor 17 and an ECG unit 18. The ECG sensor 17 is attached to the surface of the body of the subject 200, and detects an ECG signal of the subject 200 as an electric signal (hereinafter referred to as a sensor signal). The ECG unit 18 subjects the sensor signal to various kinds of processing, including digitization, and then outputs it to the host computer 16 and the sequencer 10. For example, a vector electrocardiograph can be used as the electrocardiograph unit. The sequencer 10 uses the sensor signal generated by the electrocardiograph unit, when it is necessary to carry out a scan in synchronization with the cardiac phase of the subject 200.

FIRST EMBODIMENT

The operation of the MRI apparatus 100 configured as described above in a first embodiment will next be described. It is to be noted that the MRI apparatus 100 can perform various kinds of imaging achieved by existing MRI apparatuses, which is, however, not described. Here, an operation in the case of obtaining hybrid MRA is explained.

Figure 2:
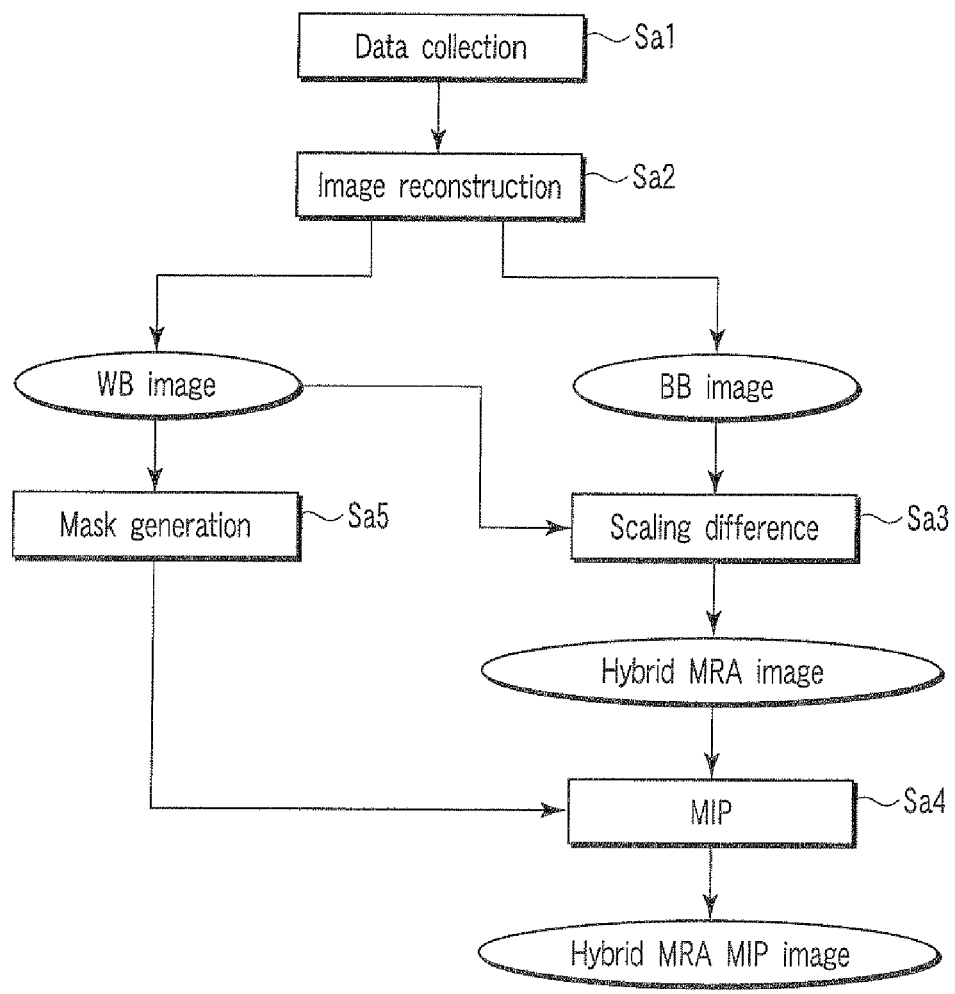
FIG. 2 is a flowchart showing a procedure for operating the MRI apparatus shown in FIG. 1 when hybrid MRA is carried out.

FIG. 2 is a flowchart showing a procedure for operating the MRI apparatus 100 when the hybrid MRA is obtained.

In step Sa1, the sequencer 10 controls the gradient power supply 7, the transmitter 9T and the receiver 9R to collect data in both a WB method and a BB method. The data collection in the WB method and the data collection in the BB method may be carried out in separate sequences, but a multi-echo method is used here to carry out the data collection in both the NB method and the BB method in a series of sequences. The data collection is carried out for each of a plurality of slices in a slab set as an imaging region.

It is optional which method is to be specifically employed as the WB method and the BB method. However, here, a TOF method is used as the WB method, and a flow-sensitive BB (FS-BB) method is used as the BB method. In addition, the FS-BB carries out data collection in a pulse sequence based on a gradient echo (GRE) including a dephase gradient magnetic field pulse. The dephase gradient magnetic field pulse generates a gradient magnetic field for emphasizing a signal decrease due to flows in arteries and veins in a region of interest.

When the pulse sequence is GRE and the strength of a static magnetic field is 1.5 T, TE is less than 10 in the case of the TOF method and 20 in the case of the FS-BB method.

Figure 3:
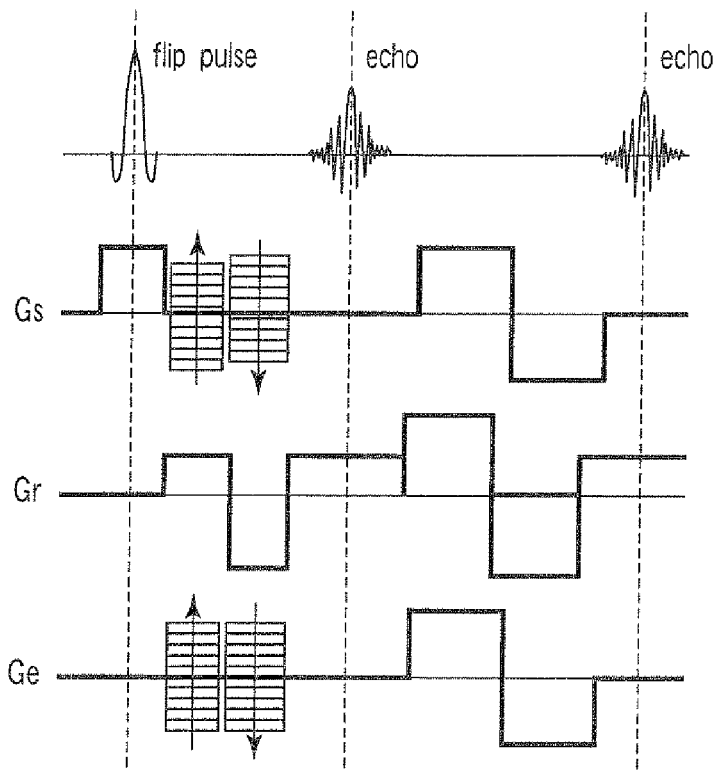
FIG. 3 is a diagram showing one example of a pulse sequence when data collection in a TOF method and an FS-BB method is carried out with two echoes.

FIG. 3 is a diagram showing one example of a pulse sequence in this case. Waveforms shown in FIG. 3 indicate, from top to bottom, a high-frequency flip pulse applied to the subject 200 and echo signals (Echo) generated in the subject 200, a slice direction gradient magnetic field (Gs), a phase-encode direction gradient magnetic field (Ge) and a read-out direction gradient magnetic field (Gr).

Here, the TOF method is in rephase, but the FS-BB method is in dephase.

Figure 4:
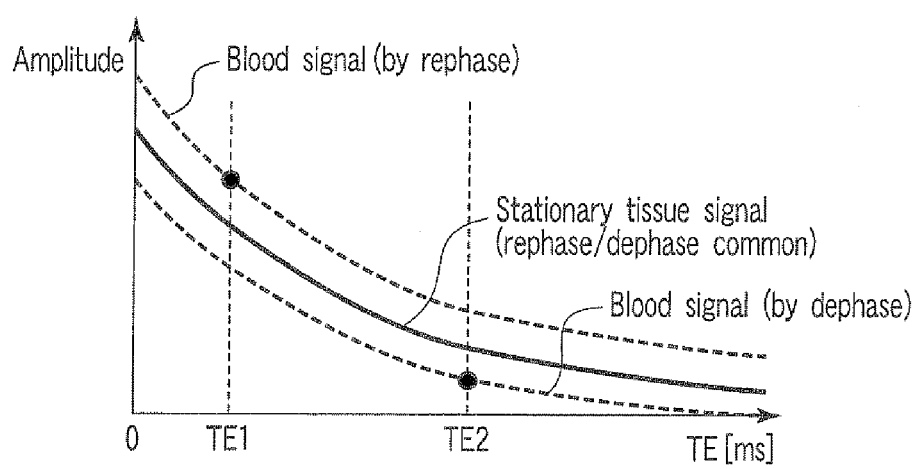
FIG. 4 is a diagram showing a change of signal intensities of intravascular blood and a stationary tissue with TE in accordance with rephase/dephase GRE sequences.

FIG. 4 is a diagram showing a change of signal intensities of intravascular blood and a stationary tissue with TE in accordance with rephase/dephase GRE sequences.

In rephase, a blood signal is collected without decreasing. On the contrary, the blood signal is collected in a suppressed manner in dephase. Thus, as shown in FIG. 3, the signal generated in the blood by rephase is higher than a signal generated in the stationary tissue. Moreover, the signal generated in the blood by dephase is lower than the signal generated in the stationary tissue.

In step Sa2, the computation unit 11 reconstructs an image in which blood vessels are indicated at higher signal intensity than the background, that is, a WB image, on the basis of the data collected by use of the TOF method as described above. The computation unit 11 also reconstructs an image in which blood vessels are indicated at lower signal intensity than the background, that is, a BB image, on the basis of the data collected by use of the FS-BB method as described above.

In step Sa3, the computation unit 11 computes a scaling difference between the WB image and the BB image. An image obtained by this computation is hereinafter called a hybrid MRA image.

Specifically, a difference value ΔS is calculated for each pixel by the following Equation (1):

$$\Delta S = S(WB) - \alpha \times S(BB) \quad (1)$$

wherein $S(WB)$ is a signal value in the WB image regarding each of the pixels associated with the same position, $S(BB)$ is a signal value in the BB image, and $\alpha$ is a scaling factor.

Figure 5:
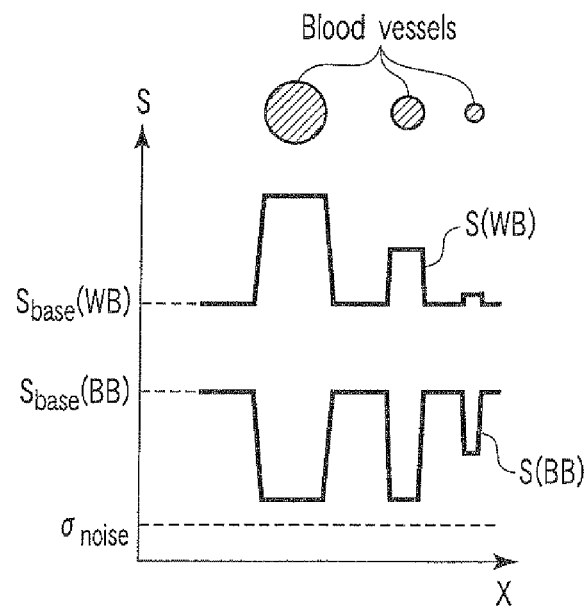
FIG. 5 is a diagram showing the relation among vessel diameters, a signal value S(WB) and a signal value S(BB)

FIG. 5 is a diagram showing the relation among vessel diameters, the signal value $S(WB)$ and the signal value $S(BB)$.

As shown in FIG. 5, the signal value $S(WB)$ related to blood vessel in the WB image is higher than a signal value $S_{base}(WB)$ of a background blood vessel. The signal value $S(BB)$ related to blood vessel in the BB image is lower than a signal value $S_{base}(BB)$ of the background blood vessel. In addition, the signal value $S_{base}(WB)$ and the signal value $S_{base}(BB)$ are generally different from each other as shown in FIG. 5 due to the differences in conditions in collecting the MR signals. Moreover, a contrast-to-noise ratio (CNR) is high in the WB image to the same extent as that in the BB image in regard to a blood vessel such as a main artery with a large diameter, but the contrast-to-noise ratio is low in the WB image in regard to a blood vessel such as a peripheral blood vessel with a small diameter. In addition, the $S_{base}(WB)$ and the $S_{base}(BB)$ can be replaced with signal intensities of low pass images of the WB image and the BB image.

Figure 6:
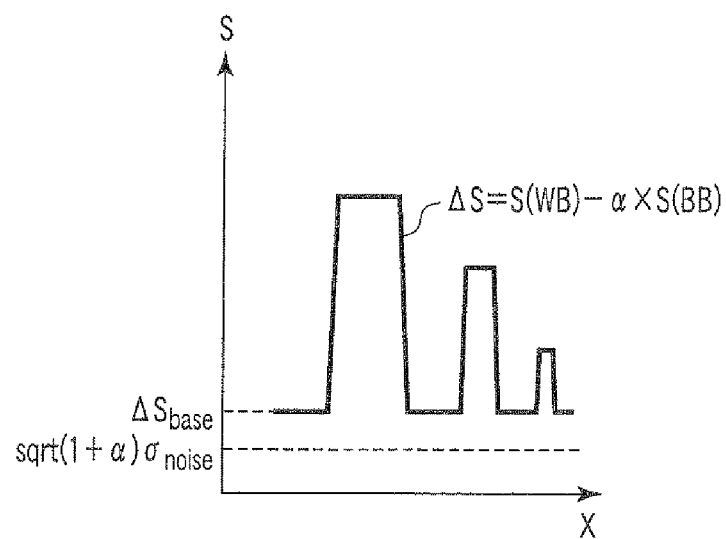
FIG. 6 is a diagram showing a difference value ΔS found from the signal value S(WB) and the signal value S(BB) shown in FIG. 5.

Thus, the difference value ΔS has higher contrast in the blood vessel, which is higher than either one of the signal value $S(WB)$ and the signal value $S(BB)$, as shown in FIG. 6.

In addition, if the scaling factor α is set so that $\alpha \times S_{base}(BB)$ does not surpass $S_{base}(WB)$, the effect of increasing the contrast can be obtained. Thus, the scaling factor α can be set to any value within the range that satisfies the above-mentioned condition. For example, a may be set to be equal to zero to eliminate weighting. However, it is preferable to set the scaling factor α so that the difference value $\Delta S_{base}$ of the background may be as close to zero as possible. The reason is that this causes the background to stand out less and can thus improve the quality of the hybrid MRA image.

Then, the hybrid MRA images mentioned above are generated for all the slices in the slab.

In step Sa4, the computation unit 11 performs MIP processing intended for a plurality of hybrid MRA images. An image obtained by this MIP processing is hereinafter called a hybrid MRA MIP image. The hybrid MRA images targeted for the MIP processing may be all or some of the hybrid MRA images for all the slices generated in step Sa3. Otherwise, the hybrid MRA images targeted for the MIP processing may include at least one hybrid MRA image in a different slice generated by multiplanar reconstruction.

In step Sa5, the computation unit 11 generates a mask image on the basis of the WB image. This mask image is an image representing a region corresponding to a cerebral parenchyma when it images, for example, blood vessels in a brain. It is difficult to extract the region of the cerebral parenchyma from the BB image because, for example, a signal difference between the cerebral parenchyma and its peripheral parts is small in the BB image. However, the cerebral parenchyma and the blood vessels have high signal intensity in the WB image, so that the regions of the cerebral parenchyma and the blood vessels can be extracted from the WB image by simple processing such as threshold processing.

The MIP processing in step Sa4 may be performed referring to the mask image so that the region corresponding to the cerebral parenchyma alone is targeted. In addition, when another image, such as an minIP image of the BB image, is displayed together with the hybrid MRA MIP image, minIP processing for this image may also be performed by referring to the mask image.

Figure 7:
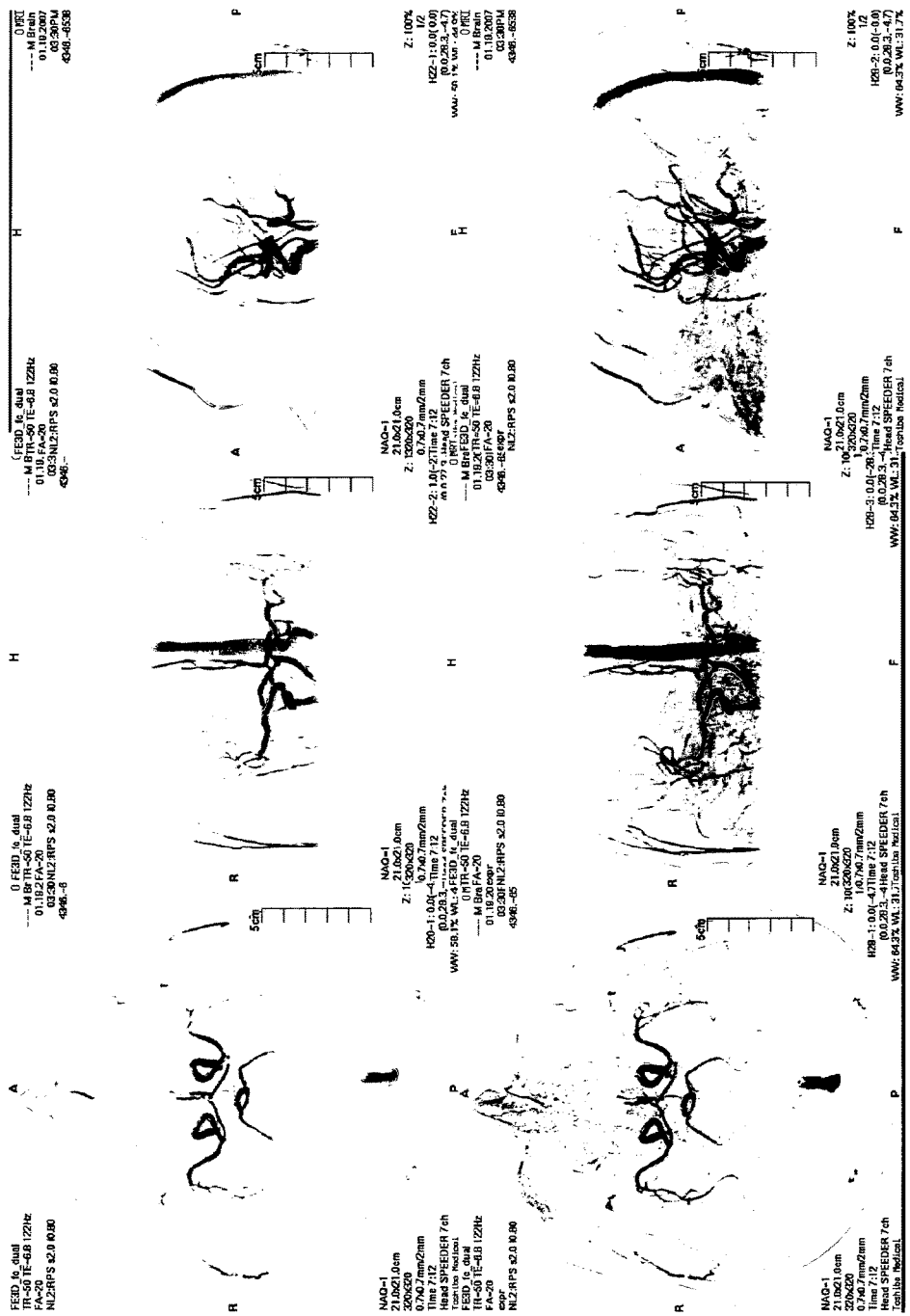
FIG. 7 is a view showing, side by side, a hybrid MRA MIP image and an MIP image of an MRA image by a conventional TOF method.

FIG. 7 is a view showing, side by side, the hybrid MRA MIP image generated in the manner described above and an MIP image (hereinafter referred to as a TOF_MRA image) of an MRA image by a conventional TOF method. In FIG. 7, the TOF_MRA image is shown on the upper side, and the hybrid MRA image is shown on the lower side. In both the TOF_MRA image and the hybrid MRA image, axial, coronal and sagittal MIP images are sequentially shown from the left.

In addition, the TOF_MRA image is imaged by 3-axis 1st order GMN in which TR=50 ms, TE=6.8 ms and FA=20 deg. The hybrid MRA is generated with α=1 in the above-described manner from the BB image imaged with TE=26 ms and b-factor=2 sec/mm² and from the above-mentioned TOF_MRA image.

As apparent from FIG. 7, the hybrid MRA image is the same WB image as the MRA image based on the TOF method, but blood vessels, especially thin peripheral blood vessels are visualized in detail with higher contrast in the hybrid MRA image than in the MRA image based on the TOF method.

Figure 8:
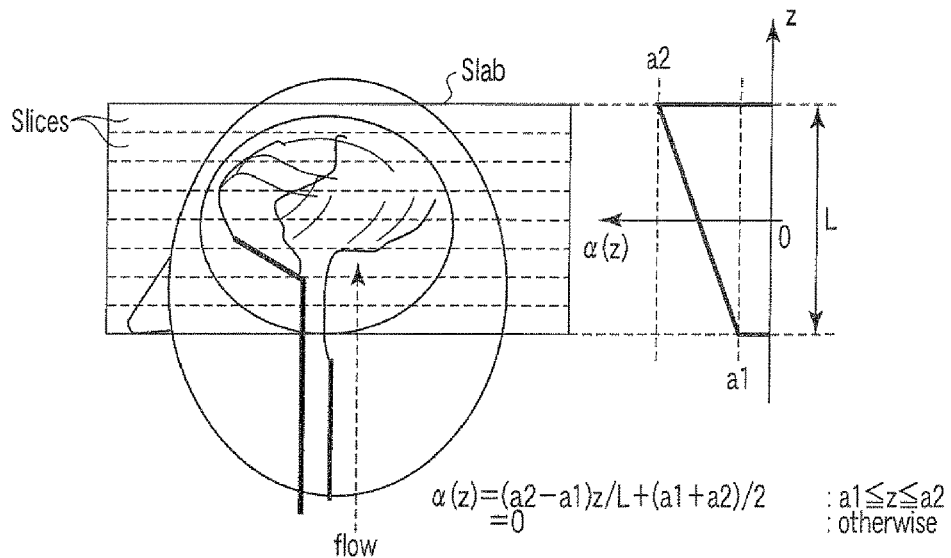
FIG. 8 is a diagram showing a specific example in which a scaling factor is set depending on a slab position.

In the TOF method, a blood vessel signal is generally large in a part where blood flows into a slab. However, it is known that the blood signals in the peripheral blood vessels are smaller because blood increases the number of times that it is continuously excited by RF as it moves into the peripheral blood vessels. Thus, if the scaling factor α applied to a slice closer to the slab inflow part is set lower than the scaling factor applied to a slice farther from the slab inflow part, it is possible to obtain a high-quality hybrid MRA image which has obtained the above-mentioned nature into account. FIG. 8 is a diagram showing a specific example in which the scaling factor is set depending on a slab position as described above.

A value optimum as the scaling factor α varies depending on the pixel in accordance with the relation between the WB image and the BB image. It is therefore preferable to set the scaling factor for each pixel and apply it to the scaling difference.

Processing for setting a scaling factor for each pixel is explained below.

In the first embodiment, the diameter of a blood vessel, the signal intensities of the WB image and the BB image or the CNR with respect to peripheral tissues are measured, and a scaling factor is adaptively set in accordance with the comparison of these measurements. The blood vessel signal has a relatively large number of high-frequency components, and the blood vessel signal can therefore be extracted by taking a difference between identical pixels in the image which has been subjected to low pass filter processing and the same image which has not been subjected to the low pass filter processing. Otherwise, the blood vessel signal can be extracted by decreasing a low-frequency background signal through high pass filter processing. A difference value thus found is more likely to indicate a blood vessel if it is greater in a positive direction in the case of the WB image and in a negative direction in the case of the BB image. As a noise component is constant, signal intensity directly indicates a CNR. It should be noted that the BB image includes more thin blood vessels than the WB image obtained by the TOF method. For this reason, the BB image includes more high-frequency components than the WB image obtained by the TOF method.

Figure 9:
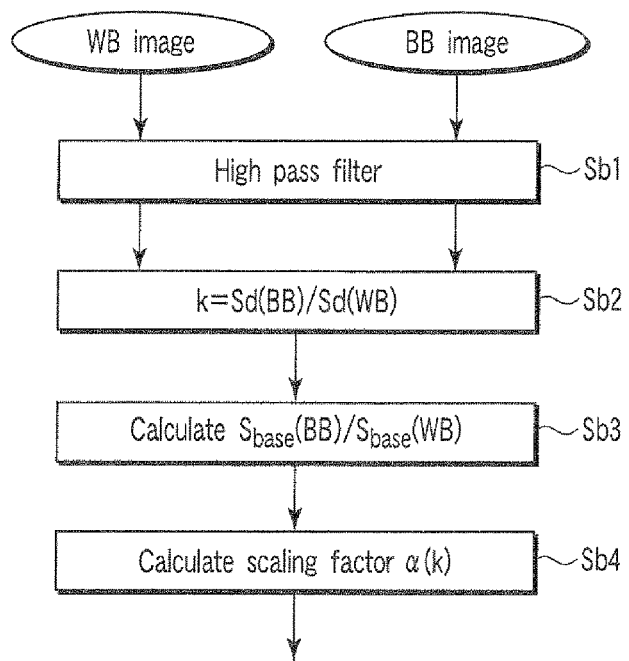
FIG. 9 is a flowchart showing a processing procedure of a host computer in FIG. 1 for setting a scaling factor for an arbitrary one pixel.

FIG. 9 is a flowchart showing a processing procedure of the host computer 16 for setting a scaling factor for an arbitrary one pixel.

This processing is performed before the scaling difference is calculated in step Sa3 in FIG. 2, on the basis of the WB image and the BB image reconstructed in step Sa2.

In step Sb1, the host computer 16 subjects the WB image and the BB image to the high pass filter is processing to decrease the background signals in both the WB image and the BB image and extract the blood signals therefrom. The filter characteristics applied to the WB image and the BB image are predetermined in such a manner that the BB image includes more frequency components than the WB image.

In addition, this high pass filter processing may be performed only on one of the WB image and the BB image. In this case, the high pass filter processing is preferably performed on the BB image to reduce low-frequency unevenness. Moreover, instead of the high pass filter processing, such processing may be performed as to find a difference between an image obtained by subjecting the WB image or the BB image to the low pass filter processing, and the WB image or the BB image. Otherwise, instead of the high pass filter processing, such processing may be performed as to find, as abs[Sorig]−abs[Slow], a difference dS between absolute value images associated with images obtained by subjecting the WB image and the BB image to the low pass filter processing. Further, a phase correction may be made after the high pass filter processing to obtain a real image. This phase correction can be made using, for example, a phase created from data in the center of the k-space.

In addition, such filter processing can correct unevenness in low-frequency components derived from, for example, the magnetic susceptibility.

In step Sb2, the host computer 16 calculates a value k corresponding to a CNR in accordance with the following Equation (2):

$$k = Sd(BB)/Sd(WB) \tag{2}$$

wherein Sd(WB) is a pixel value in an image obtained by subjecting the WB image to the high pass filter processing as described above, and Sd(BB) is a pixel value in an image obtained by subjecting the BB image to the high pass filter processing as described above.

Then, in step Sb3, the host computer 16 finds a ratio between the signal value $S_{base}(BB)$ and the signal value $S_{base}(WB)$ as $S_{base}(BB)/S_{base}(WB)$.

Subsequently, in step Sb4, the host computer 16 calculates a scaling factor α(k) corresponding to the value k found in step Sb2. Inside the blood vessel where there is a flow, Sd(WB)>0 and Sd(BB)<0, so that k<0. On the contrary, it is highly likely that k≥0 in the stationary tissue. In other words, the value k found as described above has a negative sign in a pixel corresponding to the blood vessel and has a positive sign in a pixel corresponding to the stationary tissue. Thus, if k≥0, the scaling factor α may be a value at which $S_{base}(WB)-\alpha \times S_{base}(BB)$ equals to zero, that is, the value found in step Sb3. If k<0, α(k) is increased in the positive direction as k increases in the negative direction.

α(k) in the case of k<0 is determined in the following manner in consideration of the relation between the CNR of the hybrid MRA image and the scaling factor α.

First, the relation between the CNR and CNR(ΔS) of a blood vessel in a weighted difference image ΔS=S1−α×S2 is derived when C1 and C2 are respective contrasts between two types of original images S1 and S2 and peripheral tissues $S1_{base}$ and $S2_{base}$, $\sigma n_1$ and $\sigma n_2$ each are intensity of noise SD in each respective one of the original images S1 and S2, and a CNR1 and a CNR2 are CNRs in the original images S1 and S2 respectively. From the definition of the problem, $C1=S1-S1_{base}$, $C2=S2-S2_{base}$, and ΔS=S1−α×S2. The contrast of the ΔS image can be expressed as in following Equation (3) using the contrasts of the original images:

$$C(\Delta S) = \Delta S - \Delta S_{base} \quad (3)$$
$$= \{S1 - \alpha S2\} - \{S1_{base} - \alpha S2_{base}\}$$
$$= \{S1 - S1_{base}\} - \alpha\{S2 - S2_{base}\}$$
$$= C1 - \alpha \times C2$$

The CNR, CNR(ΔS) of the blood vessel with the peripheral tissue in the ΔS image is as in the following Equation (4):

$$CNR(\Delta S)=C(\Delta S)/\sigma(\Delta S)=(C1-\alpha \cdot C2)/\sqrt{\sigma_{n1}^2+\alpha^2\sigma_{n2}^2} \quad (4)$$

Here, the CNR of the ΔS image is maximized under a condition of the following Equation (5):

$$\delta\{CNR(\Delta S)\}/\delta\alpha=(-C1\times\alpha\times\sigma_{n2}^2-C2\times\sigma_{n1}^2)/(\sigma_{n1}^2+\alpha^2\times\sigma_{n2}^2)^{3/2}=0 \quad (5)$$

$\alpha=\alpha_{opt}$ satisfying Equation (5) is found, and if the denominator is not zero, that is, this image is not a noiseless image, resulting in the following Equation (6):

$$\alpha_{opt}=-(C2/\sigma_{n2}^2)/(C1/\sigma_{n1}^2) \quad (6)$$

Especially when $\sigma_{n1}=\sigma_{n2}=\sigma_n$, Equation (4) and Equation (6) will be the following Equation (4') and Equation (6'), respectively:

$$CNR(\Delta S)=(C1-\alpha \cdot C2)/\sqrt{(1+\alpha^2)}\sigma_n \quad (4')$$

$$\alpha_{opt}=-C2/C1 \quad (6')$$

When the subject 200 is imaged with the same coil and with the same reception gain or imaged with two echoes, the $\sigma_{n1}$ and the $\sigma_{n2}$ can be regarded as the same, so that the above Equation (4') and Equation (6') are satisfied.

To sum up, the CNR concerning the contrast between the blood vessel and the peripheral tissue in the weighted difference image ΔS=S1−α×S2 of the two kinds of original images is maximized when equal to a value which has inverted the sign of the ratio of the CNRs concerning the contrast between the blood vessel and the peripheral tissue in each of the two kinds of original images.

By way of example, α may be equal to 1 if the image S1 is a WB image and the image S2 is a BB image and if the CNR1=10 and CNR2=−10. In other words, a simple difference S1−S2 may be enough to provide the maximum CNR. The CNR of the difference image in this case results in CNR=10−(10)/√2̄14.1, improving to 1.41 times the CNR before the difference. On the other hand, α should be equal to 0 if blood vessels are visualized in the WB image but no blood vessel is visualized in the image from which a difference is taken, that is, if CNR1=10 and CNR2=0. In other words, in order to provide the maximum CNR, S1 should be used as it is without taking a difference from S2.

Figure 10:
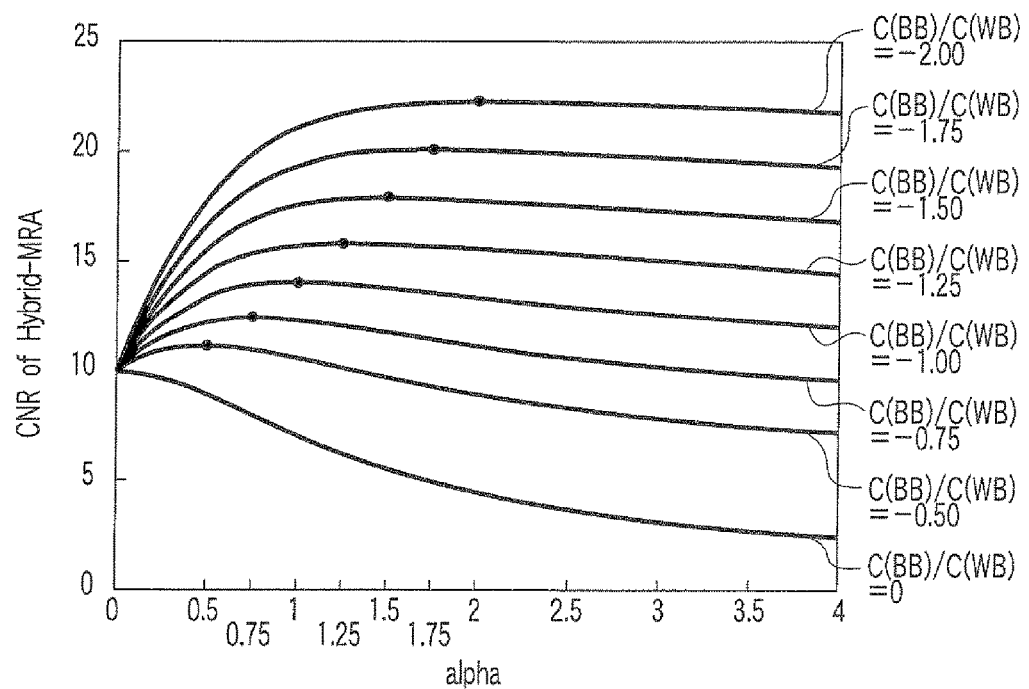
FIG. 10 is a diagram showing the relation between the CNR of a hybrid MRA image and a scaling factor α.

FIG. 10 is a diagram; showing the relation between the CNR of the hybrid MRA image and the scaling factor α.

FIG. 10 shows the relation between the CNR of the hybrid MRA image and the scaling factor α for each of the cases where the CNR of the blood vessel in the WB image is 10 and a ratio C(BB)/C(WB) between contrast C(BB) of the BB image and contrast C(WB) of the WB image is 0, −0.50, −0.75, −1.00, −1.25, −1.50, −1.75 and −2.00.

As apparent from FIG. 10, $\alpha_{opt}$ which maximizes the CNR of the hybrid MRA image is as shown in Equation (7):

$$\alpha_{opt}=-C(BB)/C(WB) \quad (7)$$

However, as apparent from FIG. 10, the CNR slightly changes with α>1 if C(BB)/C(WB)<−1.

Figure 11:
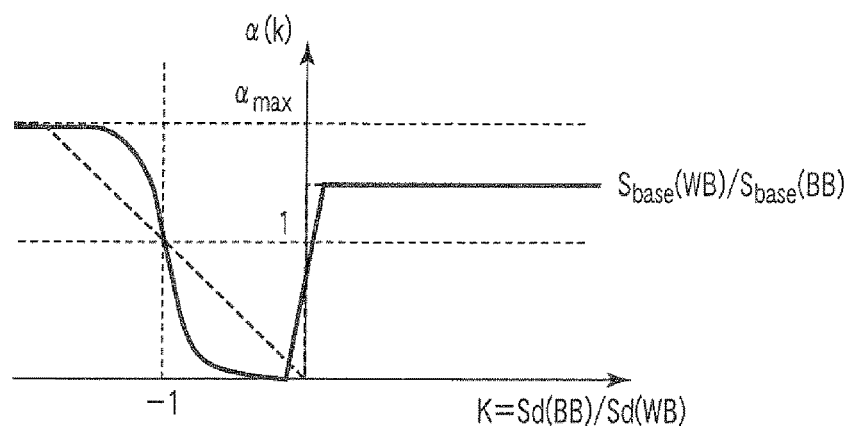
FIG. 11 is a diagram showing the relation between a scaling factor α (k) calculated by the host computer in FIG. 1 and a value k.

FIG. 11 is a diagram showing the relation between the scaling factor α(k) calculated by the host computer 16 in step Sb4 and the value k.

The host computer 16 has only to calculate the scaling factor α(k) as a value indicated by a broken line in FIG. 11 in the case of implementation following the above-mentioned logic. However, in terms of mounting, the scaling factor α(k) is smoothly changed in consideration of noise in the vicinity of k=3. In connection with this, the scaling factor α(k) should be calculated as, for example, a value indicated by a full line in FIG. 11 in the region of k<0 in order to form a natural image.

In addition, the scaling factor α is set per pixel, so that its upper limit value αmax does not have to be specifically set, but an appropriate value is set in FIG. 11 for error processing.

In addition, it is highly likely that a pixel with k>0 corresponds to the stationary tissue. Therefore, it may be replaced with the value of the corresponding pixel in the low pass filter image of the WB image or BB image or with zero in order to reduce noise in the hybrid MRA image without deriving the scaling difference.

If the scaling factor α(k) per pixel is adaptively set in this manner, it is possible to set a proper scaling factor α and generate a high-quality hybrid MRA image even when the inflow part and the thin blood vessel are not necessarily located at both ends of the slab due to complicated changes in the direction of the blood vessel.

In the meantime, there is no meaning in generating the hybrid MRA image if the CNR concerning the contrast between the blood vessel and the background is higher in the hybrid MRA image than in the WB image or BB image.

Although the CNR in accordance with TOF is higher in the main part of a blood vessel, the CNR in accordance with TOF is closer to zero in the peripheral blood vessels. Thus, the CNR concerning the contrast between the blood vessel and the background is improved if the scaling of the BB image is greater. This proves that, in the peripheral blood vessels, the BB image should be independently used without taking a difference therefrom. In that case, the CNR of the difference image is 1/√2̄=0.71 if α=1. Therefore, if the CNR of the hybrid MRA image is more than √2̄ times the CNR of the WB image or BB image, the CNR of the blood vessel is higher in the hybrid MRA image than in the WB image or BB image. Scaling by a difference so that the signal value of the background may be zero is convenient in the case of the MIP because the background is closer to zero and the difference between the background signal and the blood vessel signal is greater.

In the case of 2-echo GRE, the signal strength of the background is $S_{base}(\text{WB})>S_{base}(\text{BB})$. $\alpha>1$ in the case of a setting in which the background is zeros meaning that the peripheral blood vessels are weighted. In that case as well, since the blood vessels have to be adequately visualized by MIP without being interrupted by air in the difference image, it is desirable to provide an upper limit such as $\alpha \leq S_{base}(\text{WB})/S_{base}(\text{BB})$ so that background>air>0 is satisfied in terms of signal strength.

As described above, in the first embodiment, it is possible to visualize blood vessels at a higher CNR than in the WB image and BB image by use of the WB image in which the blood vessels are shown at higher signal intensity than the background and by use of the BB image in which the blood vessels are visualized at lower signal intensity than the background. The reduction of the signal of the background tissues is particularly important in the visualization of thin blood vessels by MIP or minIP.

Furthermore, according to the first embodiment, the capability of visualizing turbulent parts, thin blood vessels or collateral circulation is improved as compared with the TOY method. Imaging time is only slightly extended (in proportion to TR) as compared with the TOF method. Moreover, in the first embodiment, the CNR of the blood vessel with the background tissues increases, and the CNR decreases in fat and the background tissues, as compared with the TOF method. An MTC pulse necessary in the TOF method is not required in the first embodiment. In the first embodiment, the capability of visualizing turbulent parts or perforating branches is improved as compared with the TOF method.

Still further, according to the first embodiment, the CNR of the blood vessel with the background tissues increases, and the CNR decreases in the background tissues, as compared with the FS-BB method.

In addition, the use of a contrast medium may also result in WB or BB, so that the CNR of a tissue such as a blood vessel can be improved. For example, a paramagnetic contrast medium results in WB in the case of T1W and BB in the case of T2*W. Thus, data collection can be achieved by a 2-echo sequence using a GRE similar to that in the case of a non-contrast method.

SECOND EMBODIMENT

The operation of the MRI apparatus 100 in a second embodiment will next be described.

(A) Theoretical Preparation

As a theoretical preparation before the description of the specific operation, there are defined an MR signal model of a voxel with uneven magnetic susceptibility and with a flow, and rephase/dephase signal models.

(A-1) MR Signal Model of Voxel with Uneven Magnetic Susceptibility and with Flow First, parameters regarding the MR signal model of a voxel with uneven magnetic susceptibility and with a flow are defined as follows:

$M_0$: Proton density $A_{T1}$: T1 dependent attenuation $$A_{T1}=1-\exp(-TR/T1)$$

$A_{T2}$: T2 dependent attenuation $$A_{T2}=\exp(-TE/T2)$$

$A_D$: Diffusion dependent attenuation $$A_D=\exp(-bD)$$

$A_{sus}$: Susceptibility dependent attenuation $$A_{sus}\exp[-TE(\gamma \Delta B_0 \sigma)]*$$

$\Phi_{sus}$: Susceptibility dependent phase $$\Phi_{sus}=-TE(\gamma \Delta B_{0m})$$

However, in the case of Lorenzian model

T2*: Relaxation time including T2 and a component generated by a susceptibility effect $$1/T2*=1/T2+\gamma \Delta B_0(T2*<T2)$$

It is to be noted that the use of T2* leads to $A_{T2}A_{sus}=\exp[-TE/T2*]$.

$A_{flow}$: Flow dependent attenuation $$A_{flow}=\exp[-bD_{flow}]$$

b: Factor calculated from a gradient pattern defined by diffusion (gradient factor)

$D_{flow}$: Phase dispersion factor by the flow (corresponding to a factor equivalent to a diffusion factor defined by a part without flow)

Φflow: Flow dependent phase shift $$\Phi_{flow}=-\gamma \int_0^{TE} G(t) \times (t) dt$$

V: Tissue including uneven magnetic susceptibility and a flow. This is a tissue with $\Delta B_0 <>0$ and $\Phi <>0$. For example, a vein corresponds to this.

In this case, an MR signal S from the tissue V is generalized as in Equation (8):

$$S=(M_0 A_{T1} A_{T2} A_D A_{sus} A_{flow})\exp[i(\Phi_0+\Phi_{sus}+\Phi_{flow})] \quad (8)$$

Here, out of the effects of the magnetic susceptibility and the flow, coherent components are generated in a phase, and incoherent components are generated in amplitude attenuation. In other words, in the contrast, an amplitude term acts more dominantly than a phase term as $\Delta B_0$ distribution in the voxel is greater or as an intravoxel incoherent motion (IVIM) component is greater. In addition, an IVIM component is greater in the order of vein, venule and capillary vessel (A-2) Rephase/Dephase Signal Model Next, the rephase/dephase signal model is explained.

In an ideal model, components generated by the flow are cancelled in both the amplitude and the phase and components generated by the magnetic susceptibility alone are present in the case of rephase. However, changes dependent on a gradient moment nulling (GMN) order or turbulence are actually caused even in rephase. On the other hand, in the case of dephase, flow components are added to susceptibility components in both the amplitude and the phase, so that signals $S_{re}$ and $S_{de}$ in ideal models of rephase and dephase are expressed as in the following Equation (9) and Equation (10):

$$S_{re}=(M_0 A_{T1} A_{T2} A_D A_{sus})\exp[i(\Phi_0+\Phi_{sus})] \quad (9)$$

$$S_{de}=(M_0 A_{T1} A_{T2} A_D A_{sus} A_{flow})\exp[i(\Phi_0+\Phi_{sus}+\Phi_{flow})] \quad (10)$$

Here, if a repetition time TR and an echo time TE are the same in the sequence conditions of rephase/dephase and if a b factor of dephase is so small that the effect of Ad can be neglected, $S_{de}$ is as in the following Equation (11):

$$S_{de}=S_{re}A_{flow}\exp[i\Phi_{flow}] \quad (11)$$

In other words, $S_{de}$ is the addition of the flow effect to $S_{re}$. The change of the MR signal (amplitude, phase) has the following nature:

The change of the MR signal is greater as the ratio of flow components in a voxel $M_{flow}/(M_{flow}+M_{st})$ is higher.

The change of the MR signal is greater with a higher b factor.

The change of the MR signal due to an amplitude attenuation effect from a dephase grad. is greater if the IVIM component is greater.

The change of the MR signal due to a phase change effect from the dephase grad. is greater if the IVCM component is greater.

(B) Data Collection and Processing Method in Rephase/Dephase

The use of dephase in combination with rephase enables a new application in contrast with the conventional use of rephase or dephase alone. As described above, a signal change is only caused by T1 relaxation, T2 relaxation and the susceptibility effect in rephase. In dephase, the flow effect is added to the effects in rephase. Thus, data for rephase and dephase can be computed with regard to one another to obtain an image in which the flow effect is separated from the components of the effects other than the flow effect, such as components associated with the stationary tissue and the susceptibility effect. Moreover, the above-mentioned computation makes it possible to obtain a universal parameter image more quantitatively representing the magnetic susceptibility and the flow effect. Clinically, this concerns the separation of arteries from veins using the physical intensity of the flow effect and the susceptibility effect in dephase and rephase. Here, devices in collection and clinical applications thereof are provided as examples.

(B-1) Theory

The theory is explained before the explanation of a specific processing procedure.

The MR signal in rephase and dephase is a complex signal having an amplitude and a phase. If the Equations (9) and (10) are expressed as functions of an arbitrary gain K and TR, TE and the b factor, which are variable parameters of a sequence, while the gains of the MR signal are K, $A_0=M_0$, $A_{T1}$ and $A_{T2}$, the results are as shown in Equation (9') and Equation (10'):

$$S_{re}(TR,TE)=A_{re}(TR,TE)\exp[i\Phi_{re}(TE)]=KA_0(TR,TE)$$
$$A_{sus}(TE)\exp[i\{\Phi_0(TE)+\Phi_{sus}(TE)\}] \quad (9')$$

$$S_{de}(TE,TE,b)=A_{de}(TE,TE)\exp[i\Phi_{de}(TE)]=KA_0(TE,TE)$$
$$A_{sus}(TE)A_{flow}(b)\exp[i\{\Phi_0(TE)+\Phi_{sus}(TE)+_{flow}(b)\}] \quad (10')$$

In addition, here, the b factor has only to exert the signal attenuation effect caused by the flow and is therefore sufficiently small, so that an effect $A_D$ of molecular diffusion occupied in $A_0$ is negligible. In other words, $A_0$ is the same in rephase and dephase. Further, longitudinal magnetization Mz is found by $M_0$ $A_{T1}$, and $A_{T1}$ is determined by TR including an inflow effect in the case of the GRE.

(B-1-1) Living Tissue, and Magnetic Susceptibility and Flow

When the difference of nature between the magnetic susceptibility and flow is examined with respect to each tissue in a living body, much oxyhemoglobin (oxyHb) is contained and the susceptibility effect can therefore be neglected in arteries, so that arteries are not visualized in rephase. On the other hand, in veins, the flow effect is smaller than in arteries, and the susceptibility effect due to deoxyhemoglobin (deoxyHb) is added. Therefore, for blood vessels, if the phase change due to the flow is completely refocused in rephase, vein signals (susceptibility effect components) are dominantly visualized. As a result, both arteries and veins (susceptibility effect+flow components) are visualized in dephase. The stationary tissue is visualized equally in both rephase and dephase.

Veins have a low flow, and there is no good method but to utilize the susceptibility effect to selectively visualize the veins. Moreover, with rephase alone, the contrast between arteries and the stationary tissue is not sufficient, and it is therefore difficult to separate the arteries from the stationary tissue.

(B-12) Optimum sequence parameter: TE

For TE, TE=T2* is the optimum condition of TE which maximizes the CNR in both the amplitude and phase. In other words, when TE is equal to T2* of a target tissue, the maximum CNR is provided between the target tissue and its neighboring tissue having T2*. While T2* has a distribution depending on the collection condition or the kind of human tissue, blood also has the range of susceptibility which is important in the visualization of blood vessels, and white matter and gray matter can be regarded as substantially constant, so that it is substantially possible to determine TE under the above-mentioned condition when a constant voxel size is set.

(B-1-3) Separation between Flow Effect and Susceptibility Effect

If imaging parameters such as the reception gain, TR, TE and the b factor are fixed, a comparison between rephase and dephase can be made without change. However, for more quantitative indices, the flow component should be calculated from, for example, $D_{flow}$ and displayed, while the susceptibility components should be calculated from, for example, T2* or $\Delta_\chi$ and displayed. In that case, b=0 is substituted in rephase, and two or more TEs and at least three images are required.

(B-1-3-1) Quantification of Flow Effect

If an amplitude ratio and a phase difference between dephase and rephase are taken, the flow effect can be separated on the basis of Equation (11) as shown in following Equation (12) and Equation (13):

$$\text{Dephase/rephase amplitude ratio: } A(de)/A(re)=A_{flow} \quad (12)$$

$$\text{Dephase/rephase phase difference: } \Phi(de)-\Phi(re)=\Phi_{flow} \quad (13)$$

Here, the phase difference $\Phi_{flow}$ may be found by a measurement using three directions of a velocity encode pulse VENC, as in phase contrast MR angiography (PC-MRA). However, this is not very realistic and is thus omitted here, and $D_{flow}$ is found which is in a relation as shown in following Equation (14) and which represents the degree of random phase dispersion due to various flow velocities and flows in various directions.

$$A_{flow}=\exp[-b*D_{flow}] \quad (14)$$

Here, when the value b of dephase is represented by b(de), the signal intensities (amplitudes) of dephase and rephase are represented by A(de) and A(re), respectively, b=0 can be substituted for refuse. Therefore, $D_{flow}$ is calculated by following Equation $$D_{flow}[\text{mm}^2/\text{sec}]=-\ln [A(de)/A(re)]/b(de) \quad (15)$$

(B-1-3-2) Quantification of Susceptibility Effect

First, the calculation of a quantitative index of the susceptibility effect using the amplitude is explained.

An attenuation term $A_{sus}$ due to the susceptibility effect is dependent on TE, and a single TE cannot erase $A_0$ containing the contributions of, for example, the T1 relaxation and T2 relaxation. Thus, more universalization can be achieved if T2* containing $\gamma\Delta B_0\sigma$ or T2 is found.

When two TEs (hereinafter, these are referred to as TE1 and TE2, with TE2>TE1) in rephase are used, signal strengths (amplitudes) A1 and A2 in TE1 and TE2 are determined by the following Equation (16) and Equation (17):

$$A1 = KA_0 \exp[-TE1/T2^*] \quad (16)$$

$$A2 = KA_0 \exp[-TE2/T2^*] \quad (17)$$

From Equation (16) and Equation (17), the index of the amplitude attenuation effect from the susceptibility effect is expressed by the following Equation (18):

$$T2^* = (TE2-TE1)/\ln[A1(TE1)/A2(TE2)] \quad (18)$$

Furthermore, to calculate T2*, a multi-echo composed of three or more echoes may be acquired to use least mean square approximation.

On the other hand, the case of using the phase is explained.

As another expression of the susceptibility effect, $\Phi_{sus}$ is found from a phase in which a low-frequency phase component is subtracted from a single TE of rephase or from a phase difference of two echoes. $\Phi_{sus}$ for the single echo and $\Phi_{sus}$ for the two echoes are expressed by the following Equation (19) and Equation (19'), respectively:

$$\Phi_{sus} = -2\pi\gamma\Delta_\chi B_0(\cos^2\theta - 1/3)TE \quad (19)$$

$$\Phi_{sus} = -2\pi\gamma\Delta_\chi B_0(\cos^2\theta - 1/3)(TE2-TE1) \quad (19')$$

On the basis of this $\Phi_{sus}$, $\Delta_\chi$ for the single echo and $\Delta_\chi$ for the two echoes are expressed by the following Equation (20) and Equation (20'), respectively:

$$\Delta_\chi[\text{ppm}] = -\Phi_{sus}/\{2\pi\gamma B_0(\cos^2\theta - 1/3)TE\} \quad (20)$$

$$\Delta_\chi[\text{ppm}] = -\Phi_{sus}/\{2\pi\gamma B_0(\cos^2\theta - 1/3)TE(TE2-TE1)\} \quad (20')$$

The $\Delta_\chi$ can be regarded as the representation of mean susceptibility in a voxel.

Here, γ indicates a gyromagnetic ratio, and $B_0$ indicates static magnetic field strength, each of these being uniquely determined by the apparatus. However, θ includes the direction of $B_0$ and the transit angle of a blood vessel and therefore has to be measured by, for example, checking the correlation between voxels, which is more difficult than finding it from the amplitude.

In addition, as far as susceptibility distribution alone is concerned, this can be achieved with two or more levels of TE in rephase alone, and this technique is publicly known.

Figure 12:
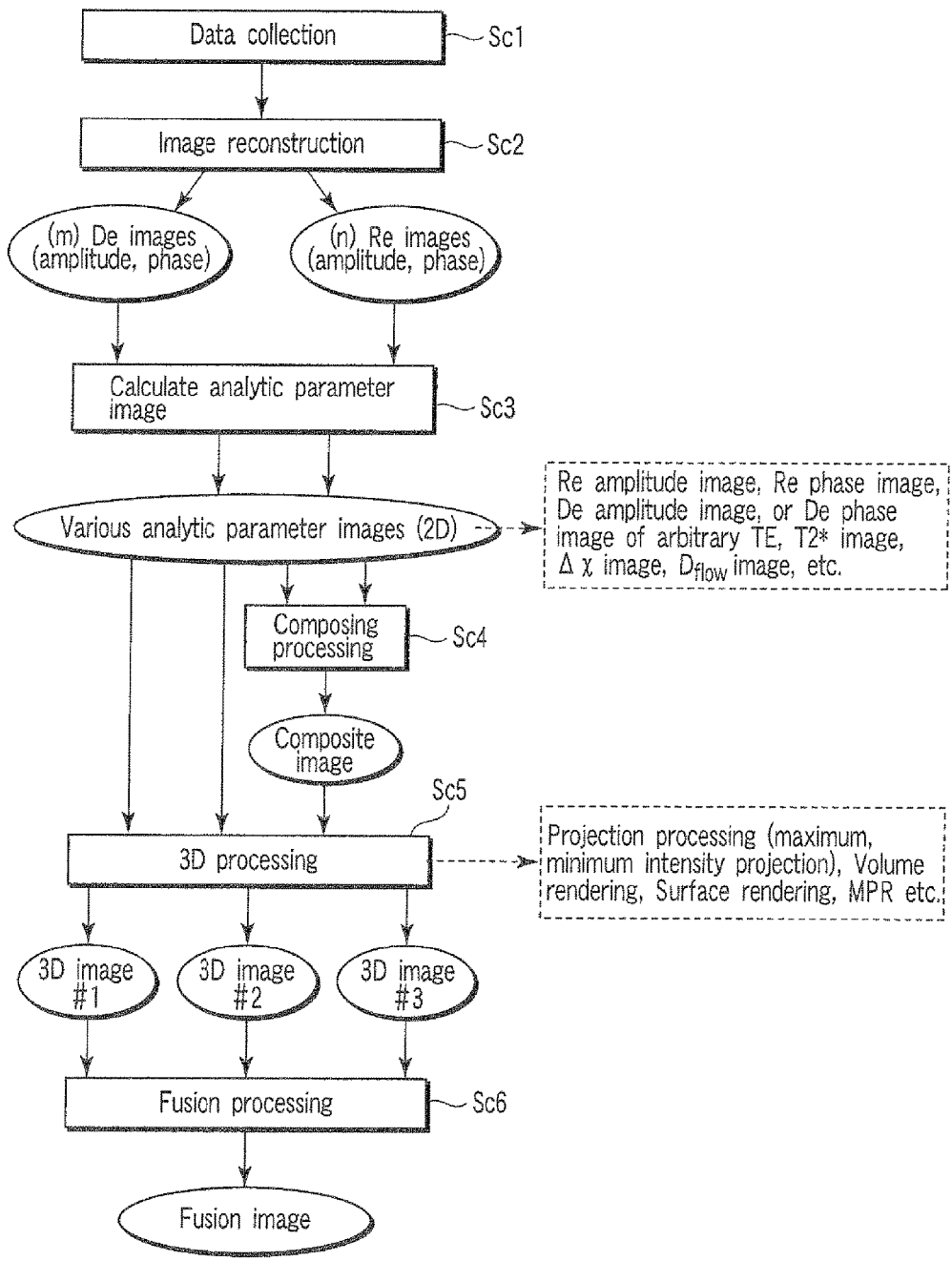
FIG. 12 is a diagram showing a processing procedure for imaging in the MRI apparatus shown in FIG. 1.

Next, the specific processing procedure is explained with reference to FIG. 12.

(B-2) Collection of Dephase Data and Rephase Data

In step Sc1, the sequencer 10 collects dephase data and rephase data.

Dephase and rephase sequences with the same TE may be independent from each other to perform sequential imaging. Otherwise, in order to minimize the effect of motion, one data set may be divided into a plurality of segments, and these segments may be alternately collected and synthesized together. Divided segments may be, for example, in a one-line (TR) unit in the k-space or in a two-dimensional surface unit.

The b factor may have a plurality of levels. The acquisition of a plurality of TEs is useful in correctly calculating T2*. A plurality of TEs can be acquired at one time by the gradient echo method if the multi-echo is collected within TR. A plurality of b factors can also be acquired at one time by use of a look-locker method. In addition, the look-locker method is known from "Measurement of Gd-DTPA dialysis clearance rates by using a look-locker imaging technique," Magn. Reson. Med., 36(4):571-8(Oct. 1996).

(B-2-1) Dephase/Rephase Alternate Divided Collection (the same TE for One Dephase/Rephase Set)

In order to calculate the flow effect $D_{flow}$ alone, the sequencer 10 collects two images for rephase and dephase with the same TE. When T2* is calculated in addition to $D_{flow}$, the sequencer 10 sets TE1 and TE2 in two echoes for rephase, and sets one of TE1 and TE2 for dephase. In that case, sequences for dephase and rephase may be divided from each other for independent imaging. Otherwise, one data set may be divided into a plurality of segments and alternately collected and synthesized together to minimize the effect of motion between images. Divided segments may be, for example, in a one-line (TR) unit in the k-space or in a two-dimensional surface unit.

(B-2-2) Rephase/Dephase Mixed Continuous Collection with GRE Multi-Echo (Different TE for each Collection)

An embodiment is shown for multi-echo processing with two or more points combining rephase and dephase by GRE.

Although the same TE cannot be used for rephase and dephase, multi-echo collection makes it possible to collect data with a plurality of TEs and uniformize the data by a calculation to obtain a quantitative parameter, as compared with the above-mentioned case of (B-2-1). A multi-echo can be acquired by one RF excitation, that is, within the same TR. This provides the greatest advantage that a scan time is about the same as the collection time for one echo. There is another advantage that an error produced between different kinds of data during computation can be reduced because a motion of the subject 200 can be neglected as compared with the case of independent collections at intervals. If items of data are collected separately, the calculation of an analytic parameter image described later can naturally be shared.

Figure 13:
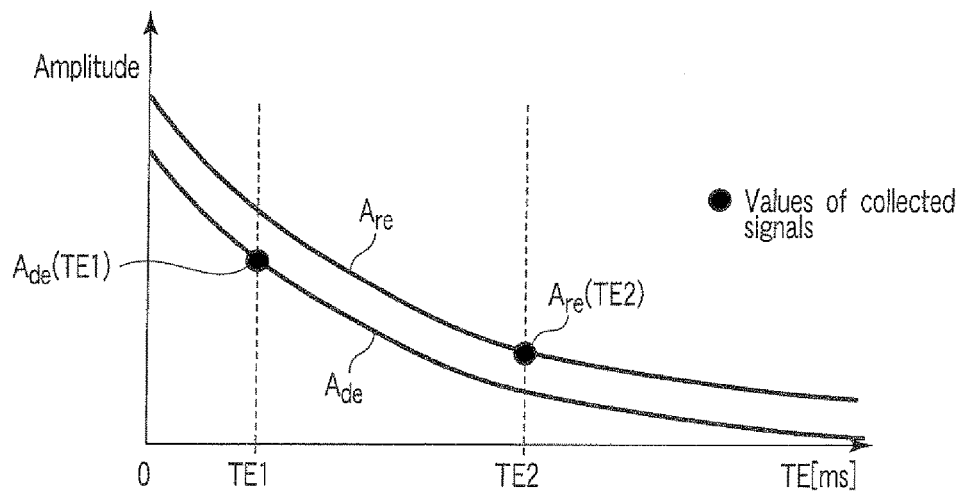
FIG. 13 is a diagram showing the relation of sample points in the case of collecting one point for a rephase TE and one point for a dephase TE.

(B-2-2-1) Two-point method (B-2-2-1-1) Collecting one point for each of rephase TE and dephase TE As shown in FIG. 13, $A_{de}$(TE1) of TE=TE1 and $A_{re}$(TE2) of TE=TE2 are separately collected.

In this case, there are no two or more points of data in the same mode, so that two images are mainly observed as they are, and T2*, $D_{flow}$, etc. in the quantitative parameter cannot be calculated. However, if the condition is set to TE2=2*TE1, the phase term $\Phi_{flow}$ of the flow alone can be quantified.

If TF(de)<TE(re), the flow is emphasized with the magnetic susceptibility suppressed in dephase, while the magnetic susceptibility is emphasized with the flow effect suppressed in rephase. If TE(re) is set shorter (<10 ms) as in TE(re)<TE(de), rephase serves as a substitute for time of flight-magnetic resonance angiography (TOE-MRA) used for collection in a normal routine for artery visualization, which may dispense with normal TOF-MRA, Moreover, dephase can be used for vein visualization emphasizing both the flow and magnetic susceptibility, and the visualization of veins can be controlled depending on the setting of TE. If phase information is used together, the CNR of veins with the background tissues can be emphasized. Further, computations can be mutually performed between dephase and rephase as described later to separately display arteries and veins. In addition, it is not necessary to strictly adapt TE for rephase to TE for dephase even in the case of two echoes, and semiquantitative display can be achieved as long as both TEs are close enough to each other and the difference of T2* is not great.

(B-2-2-1-2) Collecting two points for dephase TE

Figure 14:
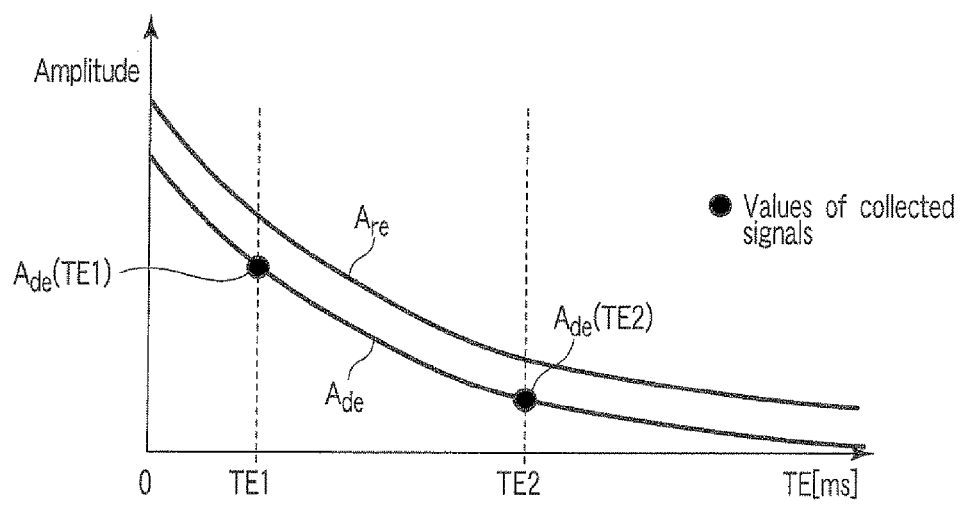
FIG. 14 is a diagram showing the relation of sample points in the case of collecting two points for the dephase TE.

As shown in FIG. 14, $A_{de}$(TE1) concerning TE=TE1 and $A_{de}$(TE2) concerning TE=TE2 are separately collected.

If the b factors of two echoes for De TE=TE1, TE2 (TE1<TE2) are the same, $A_{flow}$=exp[−b$D_{flow}$]. With the same gradient moment, $\Phi_{flow}$ is also about the same for the flow effect of the phase. Therefore, it is apparent from following Equation (21) that the flow effect is cancelled:

$$S_{de}(TE2,b)/S_{de}(TE1,b)=\exp[-(TE2/TE1)/T2^*]\exp[-i(TE2/TE1)\gamma\Delta B_{0m}] \quad (21)$$

As TE1 and TE2 are already known, it is possible to calculate T2* from the amplitude in Equation (20) and $\Delta B_0$ from the phase term, and $\Delta_\chi$ can be calculated.

(B-2-2-1-3) Collecting two points for rephase TE

Figure 15:
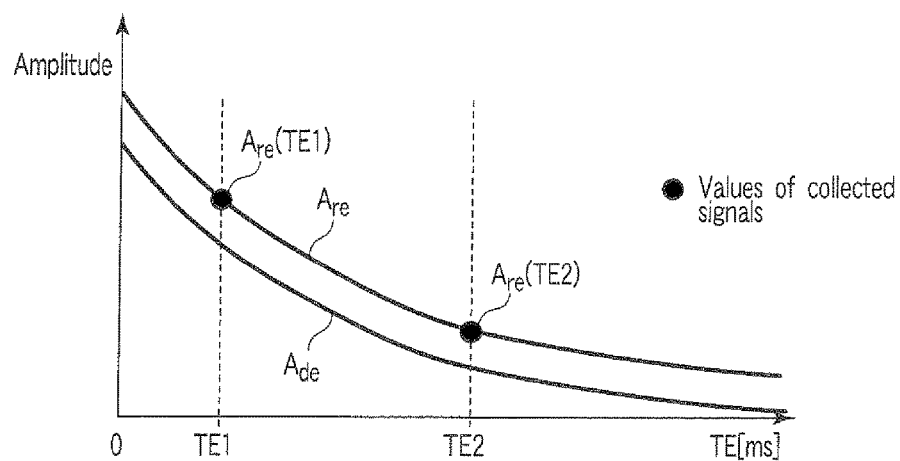
FIG. 15 is a diagram showing the relation of sample points in the case of collecting two points for the rephase TE.

As shown in FIG. 15, $A_{re}$(TE1) concerning TE=TE1 and $A_{re}$(TE2) concerning TE=TE2 are separately collected.

As it is possible to consider that b=0 with A2, the subscript de in (B-2-2-1-2) is replaced with re except that $A_{flow}$=1 and $\Phi_{flow}$=0.

(B-2-2-2) Three-Point Method

If three points are collected with rephase and dephase mixed together, it is possible to calculate a value for the flow effect in addition to T2* and $\Delta B_0$, that is, in addition to $\Delta_\chi$. Moreover, although the multi-echo for GRE is used, it is possible to generate a rephase image and a dephase image with the same TE. Any combination of three TEs may be made.

In the three-point method, there are 2×2×2=8 combinations depending on whether each echo belongs to rephase or dephase, and there are four combinations if the order is not considered. Of these combinations, two combinations are taken as examples, including a combination of rephase, rephase and dephase and a combination of dephase, dephase and rephase.

(B-2-2-2-1) Collecting two points for rephase TE and one point for dephase TE

T2* is calculated from the initial two points for rephase, and substituted for dephase of the third point to calculate $D_{flow}$. Moreover, if T2* is known from rephase, a signal of an arbitrary TE in rephase can be generated, such that rephase with the same TE as that of dephase can be found. In other words, it is possible to obtain images with the same T2 relaxation effect and susceptibility effect and with a different flow effect alone.

Figure 16:
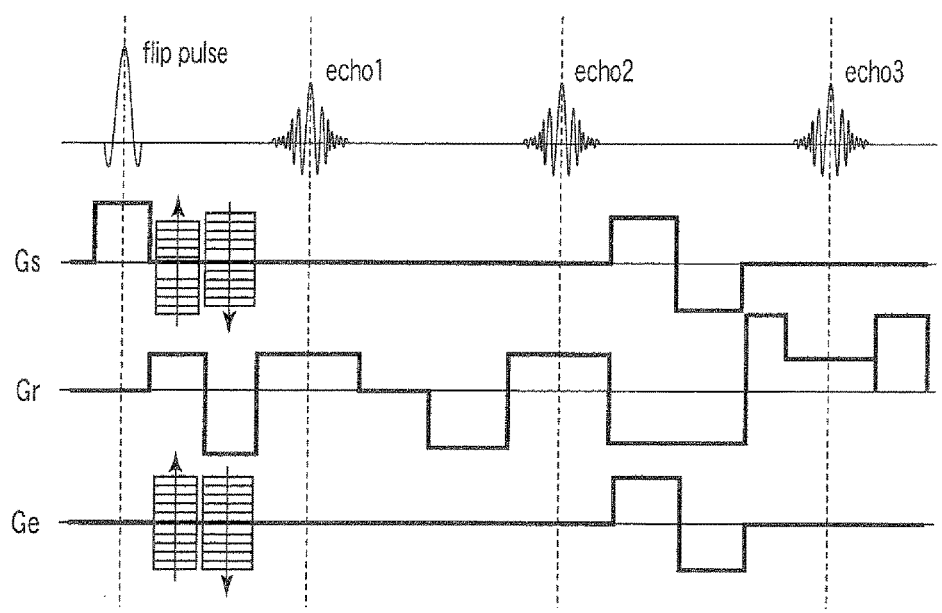
FIG. 16 is a diagram showing one example of a GRE multi-echo sequence.

One example of a GRE multi-echo sequence in this case is shown in FIG. 16.

(B-2-2-2-2) Collecting Two Points for Dephase TE and One Point for Rephase TE

As in (B-2-2-1-2) mentioned above, T2* is calculated from two points of dephase with the same initial b factor and with different TEs. Then, $D_{flow}$ is calculated from this T2* and rephase of the third point. Moreover, if T2* is known from dephase, a signal of an arbitrary TE of dephase can be generated, such that dephase with the same TE as that of rephase can be found. In other words, it is possible to obtain images with the same T2 relaxation effect and susceptibility effect and with different flow effects alone.

(B-2-2-3) Four-or-More-Point Method

Two or more points are collected for dephase and rephase, on the basis of which T2* and images with the same TE are found. Two unknown quantities and four or more points lead to least mean square approximation. Obviously, it is possible, if necessary, to calculate an unknown parameter such as M0, T2 or D.

Figure 17:
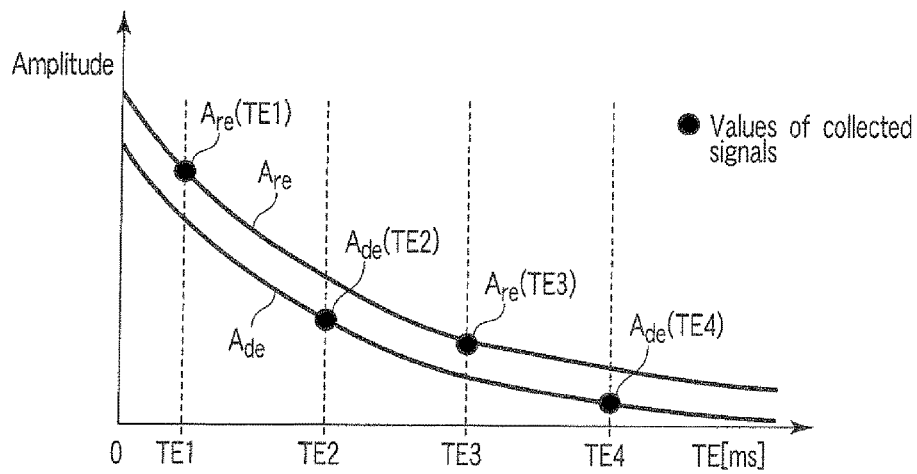
FIG. 17 is a diagram showing the relation of sample points in a four-point method.

FIG. 17 is a diagram showing one example of data collection in a four-point method, wherein $A_{re}$(TE1) concerning TE=TE1, $A_{de}$(TE2) concerning TE=TE2, $A_{re}$(TE3) concerning TE=TE3 and $A_{de}$(TE4) concerning TE=TE4 are separately collected.

In addition, in any of the various sequence modes described above, the TE of the multi-echo is set so that it includes in an optimum TE(=T2*) as used in the calculation of T2*. When the optimum TE is not easily set because the target T2* is too long (prolonged time, decreased SNR) or because the target T2* is too short (e.g., RF is not tuned into, a gradient magnetic field is not produced, or a sufficient b factor cannot be gained), an image of TE=T2* can be generated from an image of an arbitrary TE generated by a calculation.

Furthermore, in a phase calculation, it is preferable that no fold be present in all cases or that folds be corrected. In the GRE multi-echo as well, it is not necessary to strictly adapt TE for rephase to TE for dephase, and semiquantitative display can be achieved as long as both TEs are close enough to each other and the difference of T2* is not great. The sequence is not limited to GRE, and, for example, the k-space may be divided into segments by multi-shot echo planar imaging (multi-shot EPI) in which an effective TE is changed in several steps after one RF excitation, thereby properly controlling a reduction in time and an increase in resolution.

Still further, it is important to set TE to be in phase with water and fat in a tissue in which water and fat are mixed. A phase difference between water (proton) and a substance with a chemical shift of 6 ppm under the strength of a static magnetic field is expressed as $\Delta\phi=2\pi\gamma\delta B_0 TE$. The condition for these to be in phase with each other is $\delta\phi=n2\pi$, with n being an integral number, so that it should be set to a multiple of $TE=n/(\gamma\delta B_0)$. This matters little because the cerebral parenchyma does not contain much fat, but may matter in a marrow or abdominal organ in which water and fat are mixed in a voxel, for which a condition is required. If $\gamma$=42.6 MHz/T for water, $\gamma$=3.6 ppm for fat, and $B_0$=1.5T, then TE=n 4.3 ms. Moreover, a phase difference is produced if a substance with different susceptibility other than fat is mixed in the voxel, but a chemical shift due to an oxygen concentration is brought to about $\delta$=0.1 ppm, so that random selection of TE matters little in T2* in which a quantification parameter is the amplitude. This can matter in a phase in the case of strict quantification, so that, if necessary, $\delta$ is set to a known value to find and correct a phase attributed to its contribution.

(5-3) Image Reconstruction

In step Sc2, the computation unit 11 performs known reconstruction processing using data collected by the properly adopted various methods mentioned above, in order to reconstruct m dephase images and n rephase images. In addition, the values of m and n are integral numbers including 0, and are determined by the data collection technique to be employed.

(B-4) Calculation of Analytic Parameter Image

In step Sc3, the computation unit 11 calculates an analytic parameter image using 1 to n dephase images and 1 to n rephase images that have been reconstructed.

Figure 18:
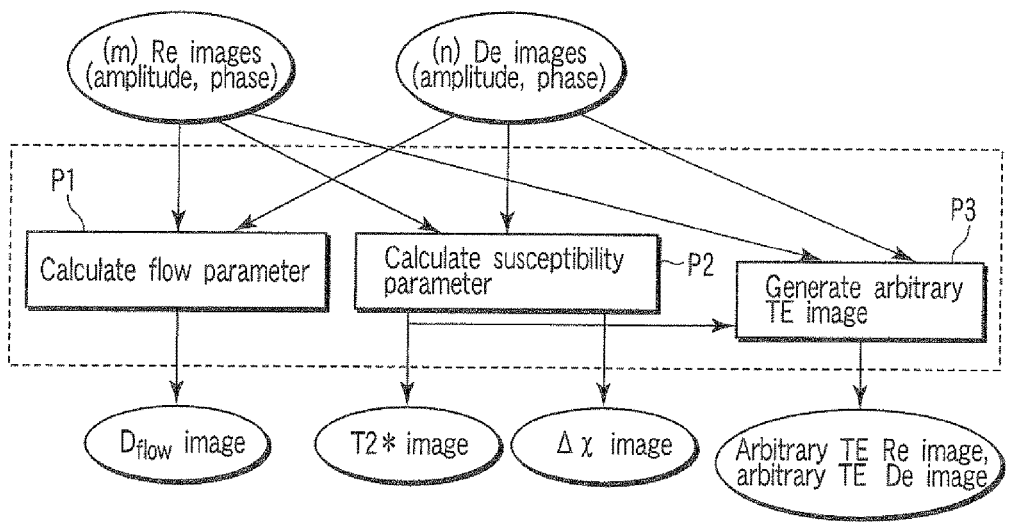
FIG. 18 is a diagram showing the concept of analytic parameter image calculating processing.

FIG. 18 is a diagram showing the concept of analytic parameter image calculating processing.

The computation unit 11 performs flow parameter calculating processing P1 using the rephase images and the dephase images to calculate a $D_{flow}$ image. The computation unit 11 performs susceptibility parameter calculating processing 22 using the rephase images and the dephase images to calculate a T2* image and a $\Delta_\chi$ image. The computation unit 11 performs arbitrary TE image creating processing P3 using the rephase images, the dephase images and the T2* image to calculate a rephase image and a dephase image concerning an arbitrary TE.

A specific example of the analytic parameter image calculating processing corresponding to each of the above-mentioned various data collection methods is explained below.

(B-4-1) Two-Point Method
(B-4-11) Case of Two Points for Dephase (a) The computation unit 11 calculates T2* and $K_{de}$ by the following Equation (22) and Equation (23) from an amplitude image A1(TE1) for TE=TE1 and an amplitude image A2(TE2) for TE=TE2 that are associated with dephase with the same b factor:

$$T2=(TE2-TE1)/\ln[A_{de}(TE1)/A_{de}(TE2)] \quad (22)$$

$$K_{de}=A_{de}(TE1)/\exp[-TE1/T2^*] \quad (23)$$

(b) The computation unit 11 calculates a dephase amplitude and a phase in association with an arbitrary TE by the following Equation (24) and Equation (25):

$$A_{de}(TE)=K_{de}\exp[-TE1/T2^*] \quad (24)$$

$$\Phi_{de}(TE)=(TE/TE1)\Phi_{de}(TE1) \quad (25)$$

(B-4-1-2) Case of Two Points for Rephase (a) The computation unit 11 calculates T2* and $K_{re}$ by the following Equation (26) and Equation (27) from an amplitude image A1(TE1) for TE=TE1 and an amplitude image A2(TE2) for TE=TE2 that are associated with dephase with the same b factor:

$$T2^*=(TE2-TE1)/\ln[A_{re}(TE1)/A_{re}(TE2)] \quad (26)$$

$$K_{re}=A_{re}(TE1)/\exp[-TE1/T2^*] \quad (27)$$

(b) The computation unit 11 calculates a dephase amplitude and a phase by the following Equation (28) and Equation (29) in association with an arbitrary TE:

$$A_{re}(TE)=K_{re}\exp[-TE1/T2^*] \quad (28)$$

$$\Phi_{re}(TE)=(TE/TE1)\Phi_{re}(TE1) \quad (29)$$

That is, the equations in (B-4-1) are used so that the subscript de therein is replaced with re.

(B-4-2) Three-Point Method
(B-4-2-1) Collecting Two Points for Rephase TE and One Point for Dephase TE The flow of processing in this case is shown in FIG. 19.

(a) In step Sd1, the computation unit 11 calculates T2* and $K_{re}$ by the following Equation (30) and Equation (31) from an amplitude image $A_{re}$(TE1) for TE=TE1 and an amplitude image $A_{re}$(TE2) for TE=TE2 that are associated with rephase:

$$T2^*=(TE2-TE1)/\ln[A_{re}(TE1)/A_{re}(TE2)] \quad (30)$$

$$K_{re}=A_{re}(TE1)/\exp[-TE1/T2^*] \quad (31)$$

A T2* image can be obtained by T2* found here.

Figure 20:
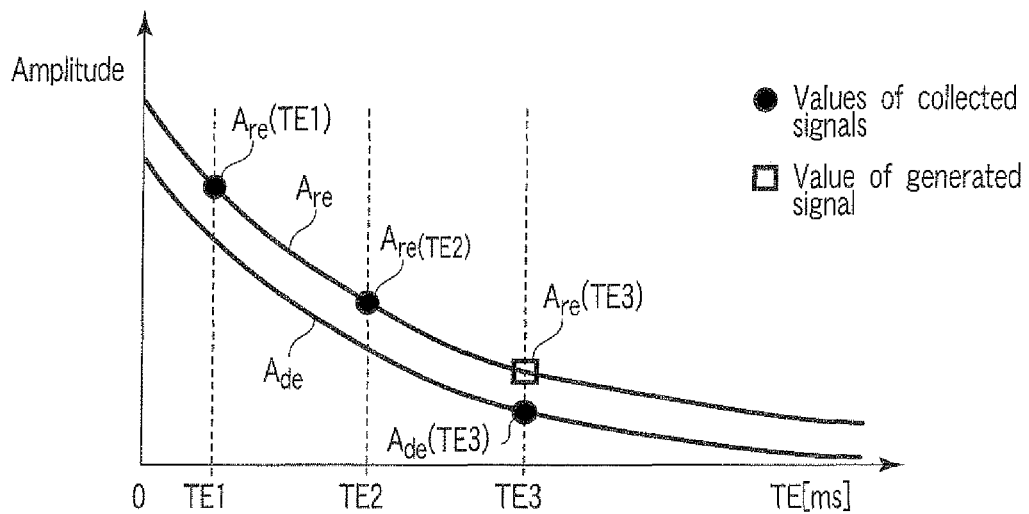
FIG. 20 is a diagram showing the relation between a sample point corresponding to an amplitude image created in the processing shown in FIG. 19 and sample points associated with actual collection.

(b) In step Sd2, the computation unit 11 generates an amplitude image $A_{re}$(TE3) for TE=TE3 associated with rephase by the following Equation (32), for example, as shown in FIG. 20. In step Sd3, the computation unit 11 generates a phase image $\Phi_{re}$(TE3) by the following Equation (33) when there is no background phase which is not dependent on TE or by the following Equation (34) when there is a background phase which is not dependent on TE:

$$A_{re}(TE3)=K_{re}\exp[-TE3/T2^*] \quad (32)$$

$$\Phi_{re}(TE3)=(TE3/TE1)\Phi_{re}(TE1) \quad (33)$$

$$\Phi_{re}(TE3)=\{TE3/(TE2-TE1)\}\cdot\{\Phi_{re}(TE2)-\Phi_{re}(TE1)\} \quad (34)$$

In addition, in step Sd2 and step Sd3, the computation unit 11 can also generate an amplitude image and phase image of rephase in which TE 1s an arbitrary value that is neither TE1, TE2 nor TE3. This can be achieved by calculating so that an arbitrary desired TE is substituted for TE3 in the above Equations (25) to (27).

(c) In step Sd4, the computation unit 11 calculates a flow dispersion factor $D_{flow}$ image from the amplitude images $A_{re}$(TE3) and $A_{de}$(TE3) for TE=TE3 by the following Equations (35) and (36):

$$A_{flow}=A_{de}(TE3)/A_{re}(TE3) \quad (35)$$

$$D_{flow}[mm^2/sec]=-\ln[A_{flow}]/b_{de} \quad (36)$$

(d) In step Sd5, the computation unit in calculates a direction angle θ between a blood vessel and $B_0$.

(e) In step Sd5, the computation unit 11 further calculates $\Delta_\chi$ [ppm] from θ and a rephase phase image of TE=TE3 by the following Equation (37):

$$\Delta_\chi[ppm]=-\Phi_{re}(TE3)/\{2\pi\gamma B_0(\cos^2\theta-\tfrac{1}{3})TE3\} \quad (37)$$

A $\Delta_\chi$ image can be obtained by $\Delta_\chi$ found here.

(f) In step Sd6, the computation unit 11 generates an amplitude image of dephase with an arbitrary TE.

The amplitude image of dephase with an arbitrary TE is calculated using the $A_{flow}$ found by Equation (35), by the following Equation (38):

$$A_{de}(TE)=A_{re}(TE)A_{flow} \quad (38)$$

In step Sd7, the computation unit 11 calculates a phase image of dephase with an arbitrary TE using $\Phi_{de}$(TE3) by the following Equation (39). This car only be calculated when there is no background phase which is not dependent on TE.

$$\Phi_{de}(TE)=(TE/TE3)\Phi_{de}(TE3) \quad (39)$$

In addition, various parameters found in the above Equations (c) to (f) may be calculated only when necessary.

(B-4-2-2) Collecting Two Points for Dephase TE and One Point for Rephase TE

Figure 21:
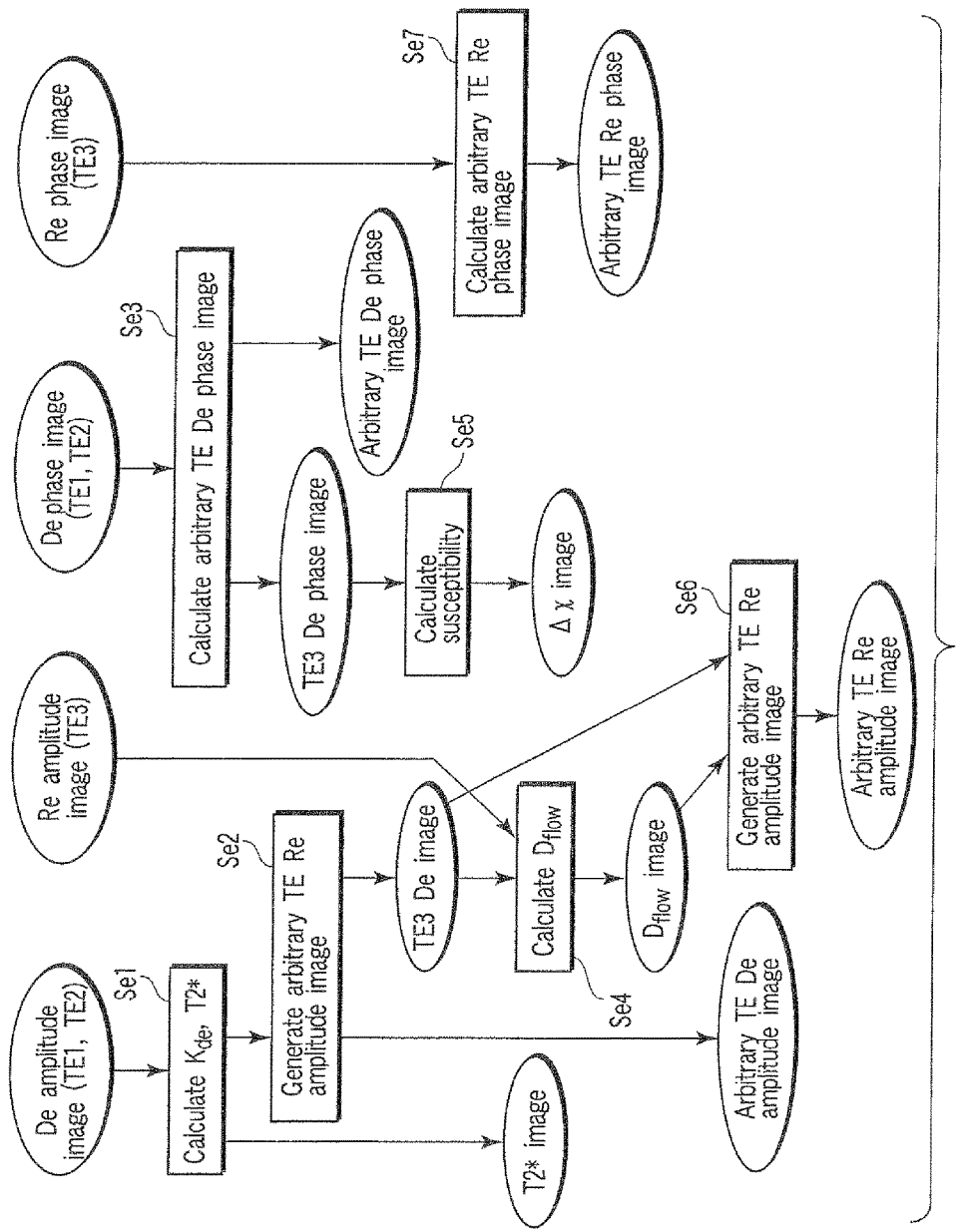
FIG. 21 is a diagram showing the flow of analytic parameter image calculating processing in the case of collecting one point for the rephase TE and two points for the dephase TE.

The flow of processing in this case is shown in FIG. 21.

(a) In step Se1, the computation unit 11 calculates T2* and $K_{de}$ by the following Equation (40) and Equation (41) from an amplitude image $A_{de}$(TE1) for TE=TE1 and an amplitude image $A_{de}$(TE2) for TE=TE2 that are associated with dephase:

$$T2^*=(TE2-TE1)/\ln[A_{de}(TE1)/A_{de}(TE2)] \quad (40)$$

$$K_{de}=A_{de}(TE1)/\exp[-TE1/T2^*] \quad (41)$$

A T2* image can be obtained by T2* found here.

Figure 22:
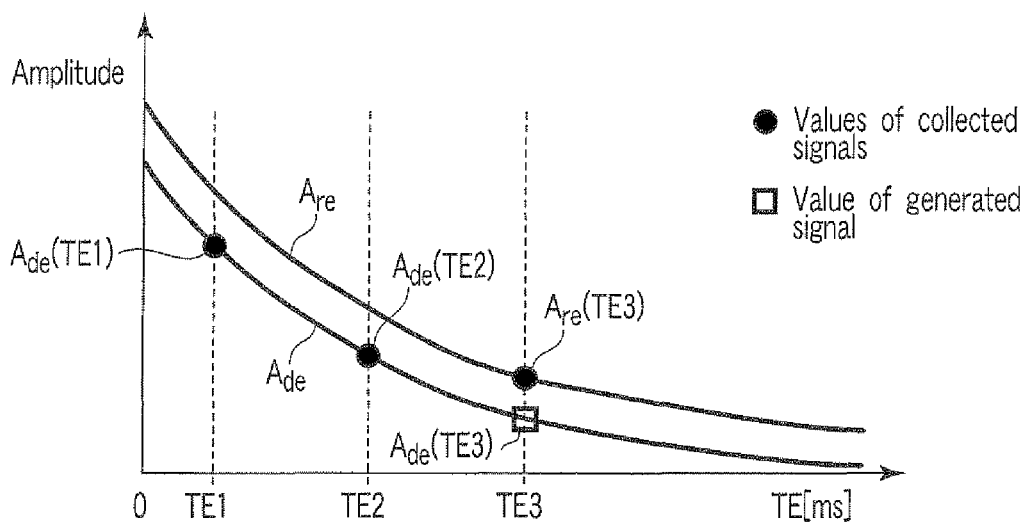
FIG. 22 is a diagram showing the relation between a sample point corresponding to an amplitude image created in the processing shown in FIG. 21 and sample points associated with actual collection.

(b) In step Se2, the computation unit 11 generates an amplitude image Ade(TE3) for TE=TE3 associated with dephase by the following Equation (42) as shown in FIG. 22. In step Se3, the computation unit 11 generates a phase image Φde(TE3) by the following Equation (43):

$$A_{de}(TE3)=K_{de}\exp[-TE3/T2^*] \quad (42)$$

$$\Phi_{de}(TE3)=(TE3/TE1)\Phi_{de}(TE1) \quad (43)$$

In addition, in step Se2 and step Se3, the computation unit 11 can also generate an amplitude image and phase image of dephase in which TE is an arbitrary value that is neither TE1, TE2 nor TE3. This can be achieved by calculating so that an arbitrary desired TE is substituted for TE3 in the above Equations (42) and (43).

(c) In step Se4, the computation unit 11 calculates a flow dispersion factor $D_{flow}$ image from the amplitude images $A_{re}(TE3)$ and $A_{de}(TE3)$ for TE=TE3 by the following Equations (44) and (45):

$$A_{flow}=A_{de}(TE3)/A_{re}(TE3) \quad (44)$$

$$D_{flow}[mm^2/sec]=-\ln[A_{flow}]/b_{de} \quad (45)$$

(d) In step Se5, the computation unit 11 calculates a direction angle θ between a blood vessel and $B_0$.

(e) In step Se5, the computation unit 11 further calculates $\Delta_\chi$ [ppm] from θ and a phase image of TE=TE3 by the following Equation (46):

$$\Delta_\chi[ppm]=\Phi_{re}(TE3)/\{2\pi\gamma B_0(\cos^2\theta-\tfrac{1}{3})TE3\} \quad (46)$$

A $\Delta_\chi$ image can be obtained by $\Delta_\chi$ found here.

(f) In step Se6, the computation unit 11 generates an amplitude image of rephase with an arbitrary TE.

The amplitude image of rephase with an arbitrary TE is calculated using the $A_{flow}$ found by Equation (44), by the following Equation (47):

$$A_{re}(TE)=A_{de}(TE)A_{flow} \quad (47)$$

In step Se7, the computation unit 11 calculates a phase image of rephase with an arbitrary TE using $\Phi_{re}(TE3)$ by the following Equation (48). This can only be calculated when there is no background phase which is not dependent on TE.

$$\Phi_{re}(TE)=(TE/TE3)\Phi_{re}(TE3) \quad (48)$$

In addition, parameters found in (c) to (f) may be calculated only when necessary.

Furthermore, in the case of three or more points for each of rephase and dephase, an unknown parameter is calculated by the least squares method in accordance with a model. The model of a linear exponential attenuation function may be used for $K_{re}$, $K_{de}$ and T2*, and the model of a linear function may be used for $\Delta_\chi$.

As described above, at least one rephase image and at least one dephase image (each including the amplitude image and the phase image), the T2* image, the $\Delta_\chi$ image, $D_{flow}$ image, etc. are calculated. It is to be noted that these images are hereinafter generically referred to as the analytic parameter image.

In addition, instead of the multi-echo, echoes separately collected one by one and formed into an image may be used, Otherwise, 2D multislice collection or volume collection by 3DFT method may be used. Moreover, as the pulse sequence, an asymmetric spin echo (ASE) method may be used instead of GRE.

(B-5) Synthesis and Display of Analytic Parameter Image

After the calculation of various analytic parameter images, these analytic parameter images can be directly displayed and provided to an observation. Moreover, parameters such as $A_{flow}$, $\Phi_{flow}$ and $\Delta_{flow}$ themselves may be displayed.

For diagnostic assistance, the computation unit 11 can, in step Sc4, generate a 2D composite image in which the various analytic parameter images are separated by color, and display the 2D image as it is. This composing processing in step Sc4 may be carried out only when necessary.

Otherwise, when particularly intended for a blood vessel image, the computation unit 11r in step Sc5, performs 3D processing to express a blood vessel as a continuous tube. A typical example of this is maximum intensity projection (MIP) or minimum intensity projection (minInP). The computation unit 11 can also generate a plurality of 3D images in step Sc5 before performing fusion processing using these 3B images in step Sc6.

(B-3-1) Phase Composing Processing and Display

A function of creating a phase composite image from the rephase image and dephase image with arbitrary TE (a) A normal MR image: $So=Ao \exp[i\Phi o]$ and a low-pass-filtered MR image: $S_1=A_1 \exp[i\Phi_1]$ are generated for each of rephase and dephase.

(b) Phase Artifact Correction

A phase map of an image subjected to a low pass filter is subtracted from a phase map of the MR image of rephase by the following Equation (49):

$$\Phi=\Phi_o-\Phi_1=\arg[S]-\arg[S_1] \quad (49)$$

After the calculation of Equation (49), processing to put into $-\pi<\Phi<=\pi$ is performed by phase jump correction. In other words, Φ is replaced with Φ+π if Φ is equal to or less than −π, or Φ is replaced with Φ−π if Φ is greater than π.

In addition, Φ may be calculated by the following Equation (50) instead of Equation (49):

$$\Phi=\arg[S/S_1] \quad (50)$$

(c) Phase Masking

Figure 23:
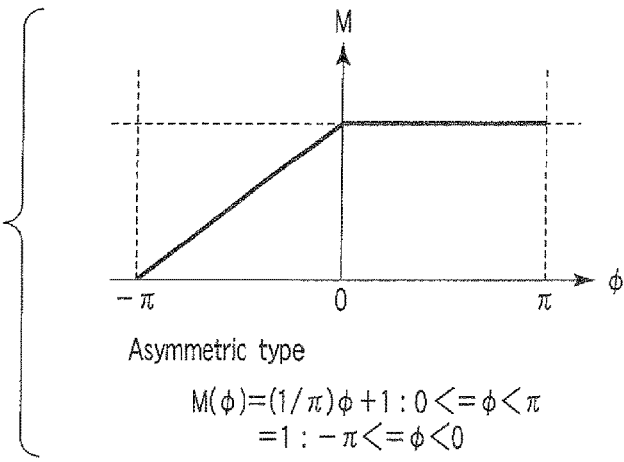
FIG. 23 is a diagram showing an asymmetric type mask.
Figure 24:
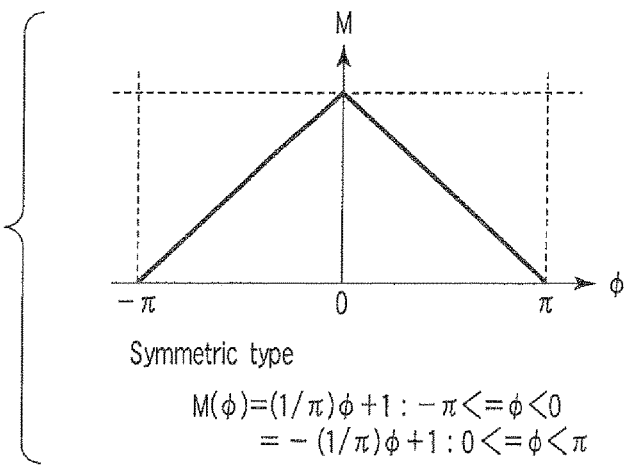
FIG. 24 is a diagram showing a symmetric type mask.

An asymmetric type mask M shown in FIG. 23 or a symmetric type mask M shown in FIG. 24 is generated, and an n-fold product I of the amplitude image and the mask M is found by the following Equation (51):

$$I=A\times M^n \quad (51)$$

In addition, a value generated from the phase of dephase is used for A, and a value generated from the phase of rephase is used for M.

This enables phase masking free of phase jumps and of phase cancellation derived from the flow and the magnetic susceptibility.

(B-5-2) Color Composing Processing and Display

Figure 25:
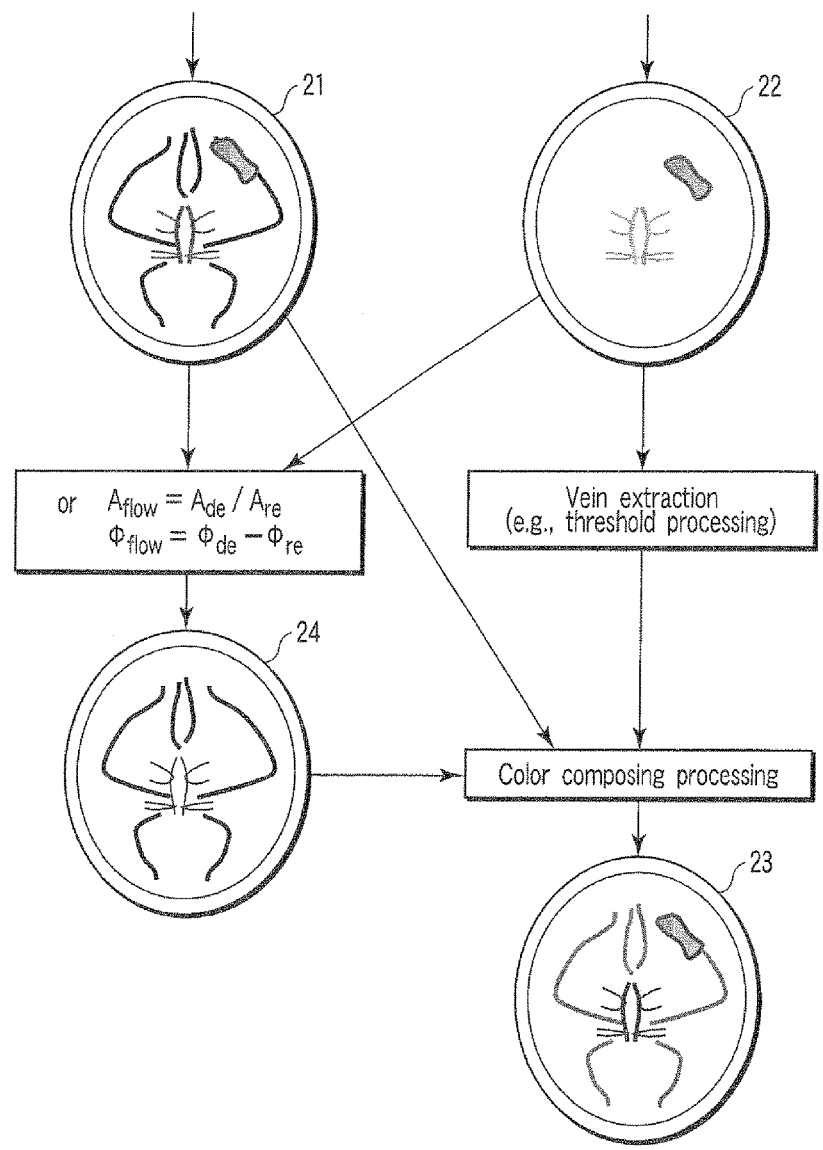
FIG. 25 is a diagram showing a specific example of color composing processing.

The analytic parameter images obtained as described above are separated by color and fusion-displayed. For example, the flow components $A_{flow}$, $\Phi_{flow}$ and $D_{flow}$ dominantly increase in arteries and veins. The susceptibility components T2* or $\Delta_\chi$ increase in veins or in, for example, a bleeding part in the case of a stationary tissue. Thus, for example, a flow component image such as an image 21 shown in FIG. 25 is classified into red, and a susceptibility component image such as an image 22 is classified into blue, and then these images are subjected to color composing processing and fusion-displayed as, for example, an image 23. The image displayed in this case is, physically, a composite image of the flow components (red) and the susceptibility components (blue). In the case of an image showing blood vessels alone, arteries are indicated in red and veins are indicated in purple. As susceptibility component parts also contain artifacts of bleeding parts or parts in which the magnetic susceptibility of the stationary tissue is not zero, these parts may be fusion-displayed after extracting veins by, for example, threshold processing if necessary.

Furthermore, an image 24 is generated in which arteries and veins are extracted from the image 21 and image 22 by the following Equation (52) or (53), and this image 24 can be color-composed with the image 22 to obtain the image 23.

$$A_{flow}=A_{de}/A_{re} \quad (52)$$

$$\Phi_{flow}=\Phi_{de}-\Phi_{re} \quad (53)$$

How the colors are mixed is decided by the ratio of the flow components with the susceptibility components. A change from red, purple to blue is shown in the above example of color allocation, and this means more flow components closer to red and more susceptibility components closer to blue. The respective colors do not necessarily correspond to the arteries and veins in the case of a disease such as cerebral infarction and serve as indices to reflect the state of oxygen metabolism. The color allocation is not limited to this, and any combination is possible as long as a contrast can be made. Although there is a method of visualizing veins by TOF-MRA, it does not visualize arteries with a slow flow in principle. The present method uses signal attenuation or a phase change caused by dephase, and can thus visualize a thin artery or a collateral circulation which runs around from an upper side, such that it is possible to provide clinically important information intended for, for example, the diagnosis of cerebral infarction. Moreover, if TE that is long to some extent is set, information on a thrombus or bleeding can also be obtained at the same time by the susceptibility effect, so that it is possible to provide information important in making a treatment plan.

In addition, a dephase amplitude image, a dephase phase image, a dephase amplitude-phase composite image or a $D_{flow}$ image, for example, can be used as the image 21. As the image 22, a rephase amplitude imager a rephase phase image, a rephase amplitude-phase composite image or a T2* image, for example, can be used.

(B-5-3) 3D Processing and Display

In the amplitude image of dephase, minIP is appropriate because both arteries and veins have lower image values than the peripheral tissues. In the amplitude image of rephase, minIP is appropriate because both veins have low signal intensity, but MIP may be used together because arteries have high signal intensity due to a TOF effect. Volume rendering or surface rendering can also be used by, for example, extracting surfaces. When original image signals are to be viewed, simply using multiplanar reconstruction (MPR) is effective depending on the purpose. The fusion display may be two-dimensionally performed as described above, but may also be performed after the creation of a 3D image.

In addition, the various images can be displayed by the display 13, but may also be displayed on, for example, an external viewer device.

As described above, according to the second embodiment, it is possible to separate and quantify the effect of the flow of, for example, blood. On the basis of the result of this quantification, information and images useful in medical diagnoses can be provided.

According to the second embodiment, it is possible to generate parameters which are not dependent on the type of a machine or sequences in terms of the magnetic susceptibility and flow. Thus, a common database can be generated, and the storage of important information as evidence is facilitated.

According to the second embodiment, arteries and veins are separated from each other by combining the rephrase and dephase.

According to the second embodiment, the use of the multi-echo makes it possible to acquire images of both rephase and dephase in one collection in contrast with the method which separately collects images of rephase and dephase, leading to reduced collection time. Moreover, a time difference among a plurality of images can be neglected, so that the effect of motion of the subject 200 is not easily produced.

According to the second embodiment, the use of two images can suppress the TOF effect of blood with a high flow velocity. For blood, contrast which is only dependent on the magnetic susceptibility or flow can be obtained.

According to the second embodiment, the collateral circulation can be visualized.

According to the second embodiment, the magnetic susceptibility and the flowcan be separated from each other.

According to the second embodiment, the amplitude image obtained by dephase has an advantage significantly important in, for example, an operation in which intravascular lumens are selectively visualized.

This embodiment can be variously modified as follows:

(a) In the first embodiment, an image is taken which is a different kind of image from the WB image and the BB image used to generate the hybrid MRA image, and this image may be composed with the hybrid MRA image to generate an image. For example, an image taken by an SWI method is useful as the different kind of image. In other words, the hybrid MRA image generated as described above serves as a WB image and mainly visualizes arteries, so that the SWI image which is a BB image showing veins can be composed (fused) with the hybrid MRA image to obtain an image showing the arteries and veins with separate colors. It is also possible to allocate different colors to the hybrid MRA image and the SWI image to generate a color image. In addition, the SWI method performs data collection with a GRE based pulse sequence including a flow compensation gradient field pulse for canceling phase dispersion of the flow after setting an echo time necessary to obtain a T2* enhanced image.

In this case, the prolongation of imaging time can be minimized if three echoes are collected by the multi-echo method. For example, when the strength of a static magnetic field is 1.5 T, TE can be less than 10 in the case of the TOF method, 20 in the case of the FS-BB method, or 40 in the case of the SWI method. Regarding SWI, GMN is desirably a rephase type to suppress arteries. In addition, although arteries and veins are mixed in the above-mentioned example of two echoes if TE in the case of the FS-BB method is about 40 ms, blood vessels can be highlighted by an arithmetical operation associated with two echoes.

(b) In the first embodiment, it is also possible to allocate different colors to the WB image and the BB image and then fuse them together to generate the hybrid MRA image. In other words, 8 bits of red and 8 bits of green are allocated to the WB image and the BB image, respectively, using, for example, RGB 24 (8×3) bits, and these images are then superposed on each other and displayed so that the colors are preserved. This provides a useful image reflecting information on the speed and oxygen concentration of each flow. For example, even with two images including the WB image and the BB image, if there is a collateral circulation on one of right and left sides, blood vessels on the side with a high flow velocity show more red, while blood vessels on the side with delay show more green. In addition, if the SWI image is additionally included as described above, blue, for example, can be allocated to this image. Thus, veins are indicated in blue.

(c) In the first embodiment, the WB image and the BB image can be obtained using a contrast medium. In the case of two echoes including T1W and T2*W with different TEs in GRE, the first echo results in WB due to a T1 reduction effect of the contrast medium, and the second echo results in BB due to the susceptibility effect.

(d) In the first embodiment, the sequence type for obtaining the WB image and the BB image as well as the SWI image is not limited to GRE, and these images may by alternately collected using an FSE based type, an echo planar imaging (EPI) based type, or a combination is of these.

(d) In the first embodiment, the generation of the hybrid MRA image (blood flow image) based on the WB image and the BB image has been described. However, the hybrid MRA image (blood flow image) may also be generated on the basis of a plurality of WB images of different kinds or a plurality of BB images of different kinds. For example, a hybrid MRA image composed of a plurality of WB images of different kinds may be generated on the basis of a non-contrast MRA image generated from data collected by a pulse sequence of the TOF method which applies a pre-saturation pulse to a position different from a region of interest, and on the basis of a T1 enhanced image obtained by use of a contrast medium. Moreover, a hybrid MRA image composed of a plurality of BB images of different kinds may be generated on the basis of an MRA image generated from data collected by a GRE based pulse sequence including a dephase gradient field pulse for emphasizing a signal decrease due to flows in arteries and veins in a region of interest, and on the basis of an MRA image generated from data collected by a GRE based pulse sequence including a flow compensation gradient field pulse for canceling phase dispersion of the flow after setting an echo time necessary to obtain a T2* enhanced image.

In the case of two WB images, Equation (13) and Equation (13') can be applied as they are because C1>0 and C2>0, wherein C1 and C2 are the contrasts of the two WB images. In the case of two BB images, Equation (13) and Equation (13') can be applied as they are because C0<0 and C2<0, wherein C1 and C2 are the contrasts of the two BB images.

(f) In the first embodiment, a hybrid MRA three-dimensional image may be generated by volume rendering to replace the hybrid MRA MIP image.

(g) In the second embodiment, when a phase mask image is generated, the amplitude of dephase may be combined with the phase of rephase, or the phase of dephase may be combined with the amplitude of rephase. This prevents the offset of the magnetic susceptibility of the phase and the flow against each other, such that vein signals in the phase mask image of the amplitude further decreases, and the resolution for arteries and vein is improved.

Figure 26:
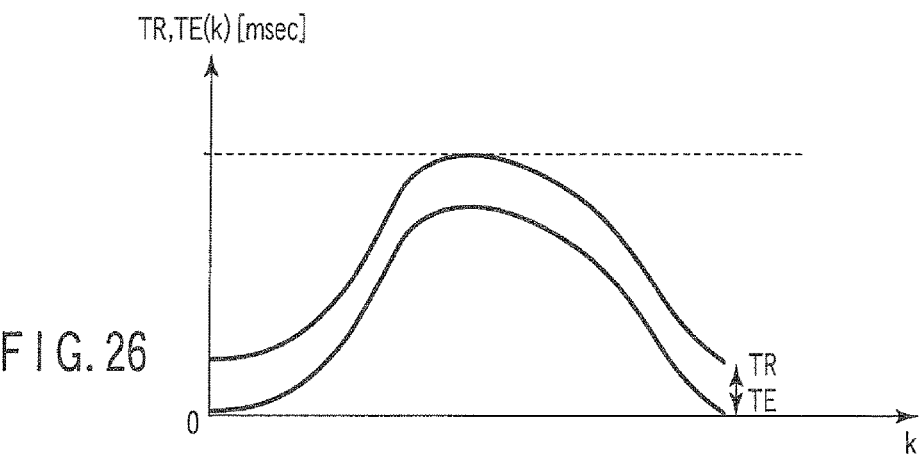
FIG. 26 is a diagram showing an example of changes of TR and TE with k.

(h) In the second embodiment, TR or TE may be varied for each frequency in the k-space to improve the imaging time and SNR. For example, during collection with a sequence, a short TE is used for low Frequencies, while a long TE is used for intermediate and high frequencies. TE is smoothly changed between these frequencies. This decreases a phase caused by an uneven static magnetic field in which low-frequency components are dominant and thus reduces artifacts. In the case of the phase, the longitudinal magnetization does not matter, and TR may thus be minimized. In addition, the sequence kind is a GRE (FE) type which is applicable to both the multi-echo and one echo, and k-space trajectory may be, for example, a spin warp, a spiral or EIP. An example of changes of TR and TE with k is shown in FIG. 26.

In addition, the magnetic resonance imaging apparatus according to each aspect of the present invention involves magnetic resonance imaging apparatuses of various aspects as shown below:

(a) The magnetic resonance imaging apparatus according to the first aspect further comprises a display unit which displays an image represented by third data.

(b) An acquisition unit in the magnetic resonance imaging apparatus according to the first aspect collects first data and second data for each of a plurality of slices, and a generation unit generates third data for each of a plurality of slices, and the magnetic resonance imaging apparatus further comprises a unit which generates a three-dimensional image on the basis of the third data on at least some of the plurality of slices.

(c) The magnetic resonance imaging apparatus according to the first aspect further comprises a unit which generates mask data corresponding to a region to be targeted for observation in a tissue of interest on the basis of one of the first data and second data, and a unit which processes the third data exclusively for the region to be targeted for observation on the basis of the mask data.

(d) The acquisition unit in the magnetic resonance imaging apparatus according to the first aspect acquires the first data and the second data by use of one of an FSE method and an EPI method or a combination of these methods.

(e) A first scan in the magnetic resonance imaging apparatus according to the third aspect carries out data collection by a pulse sequence of a TOF method which applies a pre-saturation pulse to a position different from a region of interest, and a second scan carries out data collection by a pulse sequence which obtains a T1 enhanced image by use of a contrast medium.

(f) A first scan in the magnetic resonance imaging apparatus according to the fourth aspect carries out data collection by a gradient echo based pulse sequence including a dephase gradient field pulse which emphasizes a signal decrease due to flows in arteries and veins in a region of interest, and a second scan carries out data collection by a gradient echo based pulse sequence including a flow compensation gradient field pulse in which an echo time necessary to obtain a T2* enhanced image is set and which cancels phase dispersion of a flow.

(g) A collection unit in the magnetic resonance imaging apparatus according to the fifth aspect alternately collects dephase and rephase magnetic resonance signals in the same echo time per line or surface in a 3D k-space.

(h) The collection unit in the magnetic resonance imaging apparatus according to the fifth aspect collects dephase magnetic resonance signals by a look-locker method which performs continuous collection in accordance with an echo planar imaging (EPI) method after one RF excitation.

(i) The collection unit in the magnetic resonance imaging apparatus according to the fifth aspect sets one of a plurality of echo times to T2*.

(j) A reconstruction unit in the magnetic resonance imaging apparatus according to the fifth aspect reconstructs a dephase image or a rephase image concerning an echo time different from the plurality of echo times on the basis of a plurality of dephase images or a plurality of rephase images reconstructed in accordance with the magnetic resonance signals collected in the plurality of echo times.

(k) The magnetic resonance imaging apparatus according to the fifth aspect further comprises a generation unit which generates a quantified image showing quantified characteristics, and a second quantification unit which quantifies characteristics regarding a subject on the basis of at least one of the reconstructed dephase image or rephase image, and the generation unit composes an image showing the result of the quantification by a quantification unit with an image showing the result of the quantification by the second quantification unit to generate a quantified image.

(l) The collection unit in the magnetic resonance imaging apparatus according to the fifth aspect two-dimensionally or three-dimensionally collects the magnetic resonance signals.

(m) The collection unit in the magnetic resonance imaging apparatus according to the fifth aspect collects magnetic resonance signals in the same echo time for rephase and dephase by use of a gradient echo method.

(n) The collection unit in the magnetic resonance imaging apparatus according to the fifth aspect collects magnetic resonance signals in the same echo time for rephase and dephase by use of an asymmetric spin echo method.

(o) The magnetic resonance imaging apparatus according to the fifth aspect further comprises a generation unit which generates a quantified image showing quantified characteristics, and this generation unit generates a plurality of slice images of amplitude alone, a phase alone or the composition of the amplitude and phase, and also generates a 3D quantified image by 3D processing based on the plurality of slice images.

(p) The generation unit in the magnetic resonance imaging apparatus according to the aspect of the above (o) uses sequences of different kinds for the amplitude and phase.

(q) The generation unit in the magnetic resonance imaging apparatus according to the aspect of the above (p) uses the amplitude of dephase and uses the phase of rephase.

(r) The magnetic resonance imaging apparatus according to the fifth aspect further comprises a generation unit which generates a quantified image showing quantified characteristics, and this generation unit generates a phase composite image of the rephase image and the dephase image.

(s) The magnetic resonance imaging apparatus according to the fifth aspect further comprises a generation unit which generates a quantified image showing quantified characteristics, and this generation unit generates an image in which a plurality of quantified image each showing quantified characteristics are color-composed with each other or in which an image based on the rephase image or the dephase image is color-composed with the quantified image.

(t) The generation unit in the magnetic resonance imaging apparatus according to the aspect of the above (q) generates an image in which a quantified image showing quantified flow components is color-composed with an image of susceptibility components based on the rephase image or the dephase image.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:
1. A magnetic resonance imaging apparatus comprising:
a sequencer configured to
  acquire, for a first echo time, a first background signal emanating from background tissue and a first blood vessel signal emanating from a blood vessel by performing a first sequence for a region of a subject, the first blood vessel signal being higher than the first background signal, and
  acquire, for a second echo time different from the first echo time, a second background signal emanating from the background tissue and a second blood vessel signal emanating from the blood vessel by performing a second sequence for the region of the subject, the second blood vessel signal being lower than the second background signal;
processing circuitry configured to reconstruct white blood image data by using the first blood vessel signal and the first background signal,
  reconstruct black blood image data by using the second blood vessel signal and the second background signal,
  calculate a first ratio of a second blood vessel signal value associated with the blood vessel in the black blood image data to a first blood vessel signal value associated with the blood vessel in the white blood image data, for each of pixels at corresponding positions in the white blood image data and the black blood image data,
  calculate a second ratio of a second background signal value associated with the background tissue in the black blood image data to the first background signal value associated with the background tissue in the white blood image data, for said each of pixels at corresponding positions in the white blood image data and the black blood image data,
  set a weighting factor for said each of pixels by using the first ratio and the second ratio so that a difference between the first background signal and the second background signal is reduced by applying the weighting factor to the first blood vessel signal value and/or the second blood vessel signal value,
  weight the first blood vessel signal value and/or the second blood vessel signal value by using the set weighting factor, and
  generate difference image data representing a difference between the white blood image data and black blood image data by using the weighted signal values;
  generate a difference image corresponding to the difference image data, in which a difference between a third blood vessel signal value associated with the blood vessel and a third background signal value associated with the background tissue is larger than a difference between the first blood vessel signal value and the first background signal value and then a difference between the second blood vessel signal value and the second background signal value; and
  set the weighting factor to obtain a higher contrast in the difference image data than in the white blood image data and in the black blood image data.

2. The magnetic resonance imaging apparatus according to claim 1, wherein the processing circuitry is further configured to calculate, with regard to a plurality of positions in the region, a difference between the signal values in the white blood and black blood image data for the same position in the region, thereby generating the third image data.

3. The magnetic resonance imaging apparatus according to claim 1, wherein the processing circuitry is further configured to set the weighting factor to maximize a signal-to-noise ratio in the third image data.

4. The magnetic resonance imaging apparatus according to claim 1, wherein the processing circuitry is further configured to collect the white blood image data and the black blood image data for each of a plurality of slices, and
  to set the weighting factor in accordance with the positions of the slices in a slice direction.

5. The magnetic resonance imaging apparatus according to claim 1, wherein the processing circuitry is further configured to acquire the white blood and black blood image data by use of a gradient echo method.

6. The magnetic resonance imaging apparatus according to claim 1, wherein the processing circuitry is further configured to acquire the white blood image data and the black blood image data regarding the same position by one RF excitation.

7. The magnetic resonance imaging apparatus according to claim 6, wherein the processing circuitry is further configured to acquire the white blood image data by use of gradient moment nulling (GMN), and to acquire, as the black blood image data, data to which a dephase gradient is added.

8. The magnetic resonance imaging apparatus according to claim 1, further comprising a spatial filter which is configured to reduce low-frequency components corresponding to background signals in the acquired white blood and black blood image data, or to emphasize the high frequency components corresponding to the blood vessels,
wherein the processing circuitry is further configured to generate the third image data on the basis of the white blood and black blood image data processed by the spatial filter.

9. The magnetic resonance imaging apparatus according to claim 1, wherein the processing circuitry is further configured to acquire both white blood and black blood image data by a multi-echo method while a contrast medium is put in the blood vessel.

10. A magnetic resonance imaging (MRI) apparatus comprising:
a sequencer configured to
acquire, for a first echo time, a first background signal emanating from background tissue and a first blood vessel signal emanating from a blood vessel by performing a first sequence for a region of a subject, the first blood vessel signal being higher than the first background signal, and
acquire, for a second echo time different from the first echo time, a second background signal emanating from the background tissue and a second blood vessel signal emanating from the blood vessel by performing a second sequence for the region of the subject, the second blood vessel signal being lower than the second background signal;
processing circuitry configured to
reconstruct white blood data by using the first blood vessel signal and a background signal,
reconstruct black blood data by using the second blood vessel signal and the background signal;
calculate a first ratio of a second blood vessel signal value associated with the blood vessel in the black blood data to a first blood vessel signal value associated with the blood vessel in the white blood data, for each of pixels at corresponding positions in the white blood data and the black blood data,
calculate a second ratio of a second background signal value associated with the background tissue in the black blood data to the first background signal value associated with the background tissue in the white blood data, for said each of pixels at corresponding positions in the white blood image data and the black blood image data,
set a weighting factor for said each of pixels by using the first ratio and the second ratio so that a difference between the first background signal and the second background signal is reduced by applying the weighting factor to the first blood vessel signal value and/or the second blood vessel signal value,
weight the first blood vessel signal value and/or the second blood vessel signal value by using the set weighting factor, and
generate, on the basis of a difference between the white blood data and the black blood data, third data in which the contrast of the blood vessel to the background is higher than those in the white blood and black blood data,
wherein weighting processing is performed to weight the signal values indicated in the white blood image data and black blood image data at the set weighting factor, and then to calculate the difference with regard to the white blood image data and black blood image data after being subjected to the weighting processing, the weighting factor being set to obtain a higher contrast in the blood vessel signal of the third image data than in both (a) the blood vessel signal value in the white blood image data and (b) the blood vessel signal value in the black blood image data.

* * * * *